US012178777B2

(12) United States Patent
Hall et al.

(10) Patent No.: US 12,178,777 B2
(45) Date of Patent: Dec. 31, 2024

(54) SOFT-TISSUE TREATMENT WITH NEGATIVE PRESSURE

(71) Applicant: Solventum Intellectual Properties Company, Maplewood, MN (US)

(72) Inventors: Colin John Hall, Poole (GB); Benjamin Andrew Pratt, Poole (GB); Richard Marvin Kazala, Jr., San Antonio, TX (US); Shervin Jahanian, San Antonio, TX (US); Larry Tab Randolph, San Antonio, TX (US); Jonathan G. Rehbein, San Antonio, TX (US); Tyler H. Simmons, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 911 days.

(21) Appl. No.: 16/526,792

(22) Filed: Jul. 30, 2019

(65) Prior Publication Data
US 2020/0038283 A1     Feb. 6, 2020

Related U.S. Application Data

(60) Provisional application No. 62/713,353, filed on Aug. 1, 2018.

(51) Int. Cl.
*A61H 9/00*     (2006.01)
*A61F 13/00*    (2006.01)
(Continued)

(52) U.S. Cl.
CPC ..... *A61H 9/0057* (2013.01); *A61F 13/00017* (2013.01); *A61F 13/00029* (2013.01);
(Continued)

(58) Field of Classification Search
CPC .. A61H 23/04; A61H 2205/04; A61H 9/0021; A61H 23/0218; A61H 23/0263;
(Continued)

(56) References Cited

U.S. PATENT DOCUMENTS 1,355,846 A    10/1920    Rannells
1,454,207 A     5/1923    Bemis
(Continued)

FOREIGN PATENT DOCUMENTS

AU    550575 B2    3/1986
AU    745271 B2    3/2002
(Continued)

OTHER PUBLICATIONS

International Search Report and Written Opinion for Corresponding Application No. PCT/US2019/044227, dated Dec. 18, 2019.
(Continued)

*Primary Examiner* — Ophelia A Hawthorne

(57) ABSTRACT

An apparatus for promoting circulation through a subcutaneous lymph vascular network may comprise a first manifold layer, a second manifold layer coupled to the first manifold layer, and a cover layer coupled to the second manifold layer. The first manifold may have a first stiffness, and the second manifold may have a second stiffness greater than the first stiffness. In some embodiments, the apparatus may additionally have a fluid interface configured to fluidly couple at least one of the first manifold layer and the second manifold layer to a fluid conductor through the cover layer. The fluid conductor may be coupled to or configured to be coupled to a source of negative pressure.

51 Claims, 17 Drawing Sheets

(51) Int. Cl.
*A61F 13/01* (2024.01)
*A61F 13/05* (2024.01)

(52) U.S. Cl.
CPC ........ *A61F 13/00038* (2013.01); *A61F 13/05* (2024.01); *A61H 2201/169* (2013.01); *A61H 2209/00* (2013.01)

(58) Field of Classification Search
CPC .... A61H 2201/5007; A61H 2023/0209; A61H 2201/0134; A61H 9/0078; A61M 1/962; A61M 1/91; A61M 1/915
See application file for complete search history.

(56) References Cited

U.S. PATENT DOCUMENTS

| | | |
|---|---|---|
| 1,557,978 A | 10/1925 | Cameron |
| 1,631,274 A | 6/1927 | Hubert |
| 1,671,992 A | 6/1928 | Mannborg |
| 1,726,584 A | 9/1929 | Persons |
| 1,767,320 A | 6/1930 | Oreste |
| 2,060,063 A | 11/1936 | Frimand |
| 2,324,173 A | 7/1943 | Porter |
| 2,547,758 A | 4/1951 | Keeling |
| 2,553,247 A | 5/1951 | Fowler |
| 2,609,000 A | 9/1952 | Mowbray |
| 2,632,443 A | 3/1953 | Lesher |
| 2,682,873 A | 7/1954 | Evans et al. |
| 2,816,703 A | 12/1957 | Turner |
| 2,910,763 A | 11/1959 | Lauterbach |
| 2,969,057 A | 1/1961 | Simmons |
| 3,066,672 A | 12/1962 | Crosby, Jr. et al. |
| 3,263,679 A | 8/1966 | Hass |
| 3,367,332 A | 2/1968 | Groves |
| 3,487,832 A | 1/1970 | Spence |
| 3,520,300 A | 7/1970 | Flower, Jr. |
| 3,568,675 A | 3/1971 | Harvey |
| 3,648,692 A | 3/1972 | Wheeler |
| 3,663,122 A | 5/1972 | Kitchen |
| 3,682,180 A | 8/1972 | McFarlane |
| 3,802,424 A | 4/1974 | Newell |
| 3,826,254 A | 7/1974 | Mellor |
| 3,861,217 A | 1/1975 | Rabenecker et al. |
| 3,938,514 A | 2/1976 | Boucher |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,453,538 A * | 6/1984 | Whitney ............ A61H 9/0078 128/DIG. 20 |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,870,962 A | 10/1989 | Sitnik |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,113,599 A | 5/1992 | Cohen et al. |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,439,104 B1 | 8/2002 | Tonogai et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 6,916,301 B1 | 7/2005 | Clare |
| 7,290,660 B2 | 11/2007 | Tilman et al. |
| 7,762,973 B2 | 7/2010 | Einarsson et al. |
| 7,837,387 B2 | 11/2010 | Newrones et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |

(56) References Cited

U.S. PATENT DOCUMENTS

| | | |
|---|---|---|
| 9,119,705 B2 | 9/2015 | Parish et al. |
| 9,198,801 B2 | 12/2015 | Weston |
| 9,211,365 B2 | 12/2015 | Weston |
| 9,289,542 B2 | 3/2016 | Blott et al. |
| 9,510,965 B2 | 12/2016 | Grim et al. |
| 10,383,773 B2 | 8/2019 | Han |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0173774 A1 | 11/2002 | Olsen |
| 2004/0030304 A1* | 2/2004 | Hunt ............... A61F 13/00068 604/317 |
| 2004/0215120 A1 | 10/2004 | Jensen et al. |
| 2005/0203452 A1 | 9/2005 | Weston et al. |
| 2006/0025727 A1 | 2/2006 | Boehringer et al. |
| 2006/0071965 A1 | 4/2006 | Igarashi et al. |
| 2007/0092167 A1 | 4/2007 | Tilman et al. |
| 2007/0167884 A1 | 7/2007 | Mangrum et al. |
| 2008/0199335 A1 | 8/2008 | Melatti |
| 2008/0249443 A1* | 10/2008 | Avitable ............... A61F 13/085 601/152 |
| 2008/0319362 A1 | 12/2008 | Joseph |
| 2009/0069731 A1 | 3/2009 | Parish et al. |
| 2009/0124944 A1 | 5/2009 | Ravikumar |
| 2009/0125004 A1 | 5/2009 | Shen et al. |
| 2009/0234259 A1 | 9/2009 | Hardman et al. |
| 2009/0234260 A1 | 9/2009 | Coward et al. |
| 2010/0179463 A1 | 7/2010 | Greener et al. |
| 2010/0210986 A1 | 8/2010 | Sanders et al. |
| 2010/0268198 A1 | 10/2010 | Buan et al. |
| 2011/0004168 A1 | 1/2011 | Eriksson et al. |
| 2011/0077570 A1 | 3/2011 | Findeisen |
| 2011/0112492 A1 | 5/2011 | Bharti et al. |
| 2011/0282309 A1 | 11/2011 | Adie et al. |
| 2012/0041399 A1 | 2/2012 | Blott et al. |
| 2012/0116299 A1 | 5/2012 | Tack |
| 2013/0090586 A1 | 4/2013 | Dennis |
| 2013/0123722 A1 | 5/2013 | Pratt et al. |
| 2013/0317406 A1 | 11/2013 | Locke et al. |
| 2014/0163491 A1 | 6/2014 | Schuessler et al. |
| 2014/0171837 A1 | 6/2014 | Harcourt |
| 2014/0276288 A1* | 9/2014 | Randolph ............ A61H 9/0092 601/152 |
| 2015/0011980 A1 | 1/2015 | Tan et al. |
| 2015/0080788 A1 | 3/2015 | Blott et al. |
| 2015/0320603 A1* | 11/2015 | Locke ............... A61L 31/06 604/543 |
| 2016/0213823 A1 | 7/2016 | Walborn et al. |
| 2017/0100525 A1 | 4/2017 | Heaton et al. |
| 2017/0239697 A1 | 8/2017 | Oakner et al. |
| 2018/0228653 A1 | 8/2018 | Kilpadi |
| 2018/0272052 A1 | 9/2018 | Locke et al. |
| 2018/0328353 A1 | 11/2018 | Timm |
| 2018/0353342 A1* | 12/2018 | Locke ............... A61F 13/00068 |
| 2019/0298580 A1 | 10/2019 | Hall et al. |
| 2020/0069476 A1 | 3/2020 | Randolph et al. |
| 2020/0217312 A1 | 7/2020 | Chang |

FOREIGN PATENT DOCUMENTS

| | | | |
|---|---|---|---|
| AU | 755496 B2 | 12/2002 | |
| CA | 2005436 A1 | 6/1990 | |
| CN | 104168865 A * | 11/2014 | ....... A61F 13/00068 |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| GB | 692578 A | 6/1953 | |
| GB | 2195255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/20041 A1 | 9/1994 | |
| WO | 96/05873 A1 | 2/1996 | |
| WO | 97/18007 A1 | 5/1997 | |
| WO | 99/13793 A1 | 3/1999 | |
| WO | 2010011148 A1 | 1/2010 | |
| WO | 2011008497 A2 | 1/2011 | |
| WO | 2013136181 A2 | 9/2013 | |
| WO | 2018213534 A1 | 11/2018 | |
| WO | 2018217619 A1 | 11/2018 | |
| WO | 2019002086 A2 | 1/2019 | |

OTHER PUBLICATIONS

International Search Report and Written Opinion for Corresponding Application No. PCT/US2020/025035 dated Jun. 18, 2020.
International Search Report and Written Opinion for corresponding application No. PCT/US2020/025019 dated Aug. 11, 2020.
International Search Report and Written Opinion for Corresponding Application No. PCT/US2020/025039, dated Jul. 9, 2020.
International Search Report and Written Opinion for corresponding Application No. PCT/US2020/025026, dated Aug. 24, 2020.
Chinese First Office Action Corresponding to Application No. 2020800255837, dated Apr. 25, 2022.
"Flexis Valve Labels from CCL" (https://ccllabel.com/portfolios/specialty-products-valves-labels/) 2019 CCL Industries.
Louis C. Argenta, MD and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al.; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.

(56) References Cited

OTHER PUBLICATIONS

Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and ceilified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Chinese Office Action for related application 2019800469852, dated Dec. 26, 2022.
Office Action for related U.S. Appl. No. 17/748,934, dated Apr. 5, 2023.
Office Action for related U.S. Appl. No. 17/599,229, dated Jun. 5, 2023.
Office Action for related U.S. Appl. No. 17/748,934, dated Feb. 9, 2024.
Office Action for related U.S. Appl. No. 17/748,934, dated Nov. 6, 2023.
Office Action for related U.S. Appl. No. 17/599,097, dated Nov. 8, 2023.
Office Action for related U.S. Appl. No. 17/599,229, dated Dec. 7, 2023.
Japanese Office Action for related application 2021-504262, dated Mar. 26, 2024.
Office Action for related U.S. Appl. No. 17/748,934, dated Aug. 28, 2024.
Office Action for related U.S. Appl. No. 17/599,097, dated Sep. 6, 2024.

* cited by examiner

*OUTSIDE MEASUREMENT RANGE > 2000cc/m

|  | PORT 1 (1 mm) | PORT 2 (3 mm) | PORT 3 (7 mm) | PORT 4 (15 mm) |
|---|---|---|---|---|
| SAMPLE 1 | >9.25%* | >22.82%* | >13.23%* | 22.81% |
| SAMPLE 2 | 9.36% | 5.98% | 6.14% | -3.01% |
| SAMPLE 3 | 6.54% | 5.74% | -0.125% | 2.85% |
| SAMPLE 4 | 4.12% | 4.76% | 4.5% | 2.44% |

FIG. 11

| SAMPLE 1 | PORT 1 (1 mm) | PORT 2 (3 mm) | PORT 3 (7 mm) | PORT 4 (15 mm) | COMBINED |
|---|---|---|---|---|---|
| -100 mmHg | 47.7% | 34.42% | 24.59% | 66.99% | 39.94% |
| -100 mmHg | 51.63% | 35.05% | 21.57% | 70.40% | 41.75% |
| -200 mmHg | 46.47% | 13.15% | 27.50% | 37.37% | 30.03% |

FIG. 12

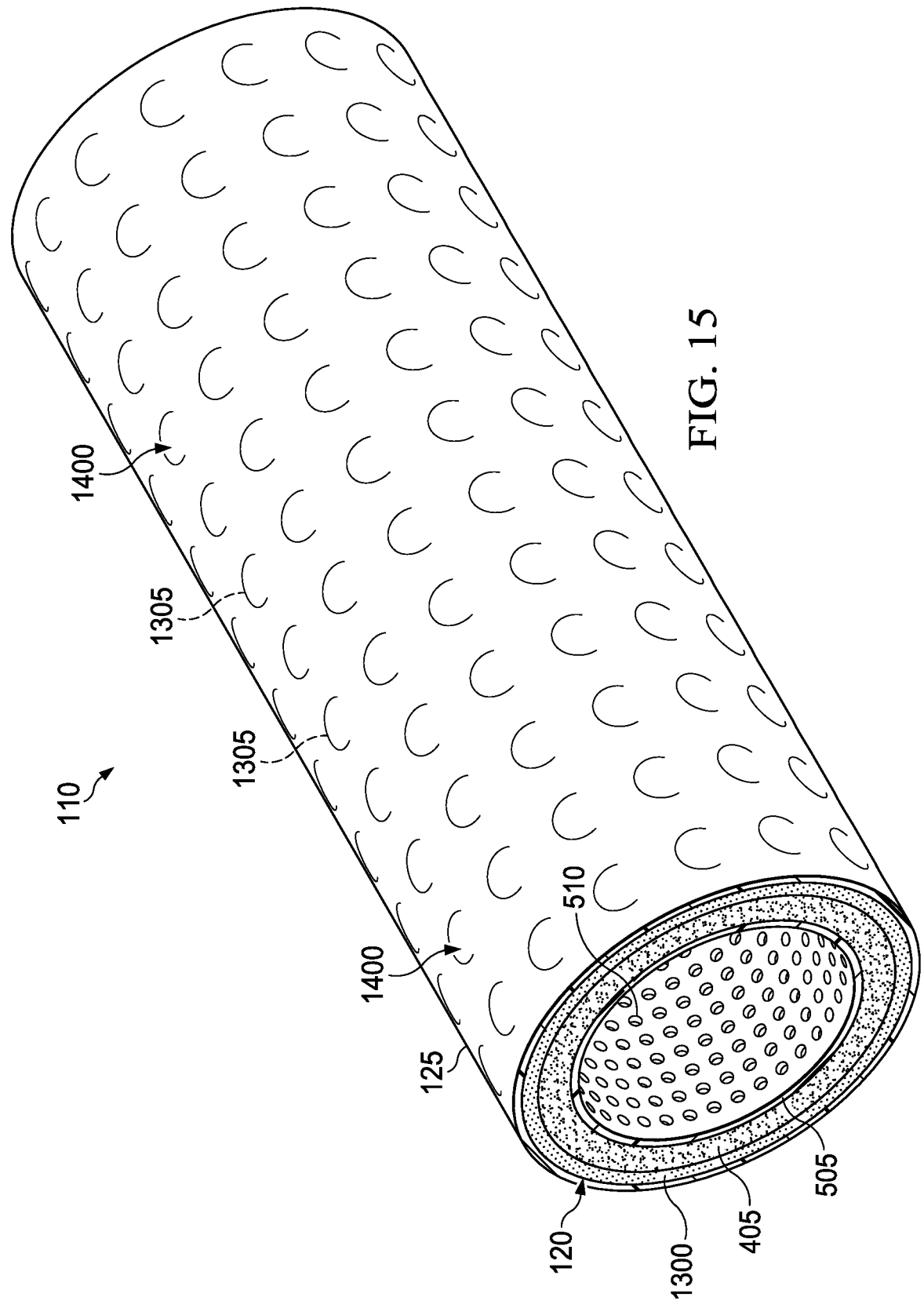

| SAMPLE NUMBER | SUPPORT LAYER 1300 | | STIFFNESS (ASTM D6828-02) (gram-force) | AVERAGE THICKNESS (mm) | DENSITY (g/cc) | WEIGHT/ UNIT AREA (g/cm²) | PERCENT IMPROVEMENT AT LYMPHATIC TEST MODEL |
|---|---|---|---|---|---|---|---|
| | MATERIAL TYPE | MATERIAL DESCRIPTION | | | | | |
| 6 | CLOSED-CELL FOAM | NEOPRENE FOAM PERFORATED WITH 6.35 MM APERTURES 25.4 MM CENTER-TO-CENTER SPACING | 1446 | 1.96 | 0.11 | 0.02 | 44.30% |
| 7 | KNIT FABRIC | PIQUE KNIT POLYESTER FABRIC | 5.5 | 0.59 | 0.21 | 0.01 | 9.06% |
| 8 | | JERSEY KNIT BLEND OF ABOUT 21% POLYESTER, ABOUT 65% NYLON, AND ABOUT 14% SPANDEX | 40.5 | 1.06 | 0.26 | 0.03 | 9.23% |
| 9 | WOVEN FABRIC | 1X1 PLAIN WEAVE BLEND OF ABOUT 65% POLYESTER AND ABOUT 35% COTTON | 12.2 | 0.30 | 0.43 | 0.01 | 10.45% |
| 10 | | 3X1 TWILL WEAVE BLEND OF ABOUT 65% POLYESTER AND ABOUT 35% COTTON | 69.9 | 0.58 | 0.47 | 0.03 | 22.27% |
| 11 | | 1X1 PLAIN WEAVE OF POLYESTER COATED WITH POLYURETHANE | 1220 | 0.93 | 0.26 | 0.02 | 38.38% |
| 12 | FILM | 8 GAUGE POLYVINYL CHLORIDE FILM PERFORATED WITH 6.35 MM APERTURES 25.4 MM CENTER-TO-CENTER SPACING | 57.3 | 0.11 | 1.14 | 0.01 | 4.56% |
| 13 | | 16 GAUGE POLYVINYL CHLORIDE FILM PERFORATED WITH 6.35 MM APERTURES 25.4 MM CENTER-TO-CENTER SPACING | 840 | 0.30 | 1.27 | 0.04 | 14.78% |
| 14 | | 20 GAUGE POLYVINYL CHLORIDE FILM PERFORATED WITH 6.35 MM APERTURES 25.4 MM CENTER-TO-CENTER SPACING | 1582 | 0.37 | 1.29 | 0.05 | 26.84% |

FIG. 18A

| SAMPLE NUMBER | SUPPORT LAYER 1300 | | STIFFNESS (ASTM D6828-02) (gram-force) | AVERAGE THICKNESS (mm) | DENSITY (g/cc) | WEIGHT/ UNIT AREA (g/cm²) | PERCENT IMPROVEMENT AT LYMPHATIC TEST MODEL |
|---|---|---|---|---|---|---|---|
| | MATERIAL TYPE | MATERIAL DESCRIPTION | | | | | |
| 15 | COMPOSITE FILM | GLASS FABRIC COATED WITH POLYTETRAFLUOROETHYLENE (PTFE) RESIN PERFORATED WITH 6.35 MM APERTURES 25.4 MM CENTER-TO-CENTER SPACING | 1490 | 0.23 | 2.10 | 0.05 | 42.09% |
| 16 | COMPOSITE FILM | GLASS FABRIC COATED WITH POLYTETRAFLUOROETHYLENE (PTFE) RESIN PERFORATED WITH 6.35 MM APERTURES 25.4 MM CENTER-TO-CENTER SPACING | 11486 | 1.45 | 0.82 | 0.12 | 43.21% |
| 17 | MESH | POLYURETHANE FOAM GRID MESH HAVING A SQUARE GRID | 222.75 | 2.57 | 0.08 | 0.02 | 4.59% |
| 18 | MESH | MULTIFILAMENT NYLON PA66 MESH HAVING A SQUARE GRID | 51.25 | 0.33 | 0.09 | 0.0029 | 20.25% |
| 19 | MESH | RESORCINOL FORMALDEHYDE LATEX COATED GLASS MESH HAVING A SQUARE GRID | 834.75 | 0.37 | 0.29 | 0.01 | 31.21% |
| 20 | NON-WOVEN | NON-WOVEN POLYESTER FABRIC | 359.5 | 2.50 | 0.11 | 0.03 | 16.46% |
| 21 | NON-WOVEN | NON-WOVEN POLYESTER FABRIC THAT HAS BEEN HEAT PRESSED FOR 1 MINUTE AT ABOUT 375 DEGREES FAHRENHEIT | 725 | 2.03 | 0.10 | 0.02 | 35.02% |
| 22 | RUBBER | ACRYLONITRILE BUTADIENE RUBBER PERFORATED WITH 6.35 MM APERTURES 25.4 MM CENTER-TO-CENTER SPACING | 282 | 0.58 | 1.53 | 0.09 | 8.44% |
| 23 | RUBBER | ACRYLONITRILE BUTADIENE RUBBER PERFORATED WITH 6.35 MM APERTURES 25.4 MM CENTER-TO-CENTER SPACING | 846 | 1.77 | 0.98 | 0.17 | 29.88% |
| 24 | RUBBER | ACRYLONITRILE BUTADIENE RUBBER PERFORATED WITH 6.35 MM APERTURES 25.4 MM CENTER-TO-CENTER SPACING | 2326 | 1.57 | 1.53 | 0.24 | 34.75% |

FIG. 18B

SOFT-TISSUE TREATMENT WITH NEGATIVE PRESSURE

RELATED APPLICATION

This application claims the benefit, under 35 U.S.C. § 119(e), of the filing of U.S. Provisional Patent Application Ser. No. 62/713,353, entitled "SOFT-TISSUE TREATMENT WITH NEGATIVE PRESSURE" filed Aug. 1, 2018, which is incorporated herein by reference for all purposes.

TECHNICAL FIELD

This disclosure relates generally to tissue treatment systems and more particularly, but without limitation, to apparatuses and systems for treating tissue with negative-pressure.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative example embodiments are also provided to enable a person skilled in the art to make and use the claimed subject matter.

In some example embodiments, a dressing for treating tissue may comprise a cuff designed to form a wrap around a limb, such as a leg or arm. Some examples of the dressing may be constructed with a felted polyurethane foam laminated to a reticulated polyurethane foam. The felted foam may form the outer layer, and the reticulated foam may form the core patient interface. The circumferentially stiffer felted foam can effectively form a more rigid shell, which can allow the softer core to reduce under negative pressure and provide an off-loading effect to a wound and surrounding tissue. The dressing may additionally include one or more of a perforated silicone, a fabric, or fenestrated film over the core in some examples. A fabric or fenestrated film can inhibit granulation, particularly if used over an incision site. The dressing may further have an adhesive-backed, breathable polyurethane film drape and a pneumatic connection to a source of negative-pressure.

Further, sin some example embodiments, an apparatus for promoting circulation through a subcutaneous lymph vascular network may comprise a first manifold layer, a second manifold layer adjacent to the first manifold layer, and a cover layer adjacent to the second manifold layer. The first manifold layer may have a first stiffness, and the second manifold layer may have a second stiffness greater than the first stiffness. In some embodiments, the apparatus may additionally have a fluid interface configured to fluidly couple at least one of the first manifold layer and the second manifold layer to a fluid conductor through the cover layer. The fluid conductor may be coupled to or configured to be coupled to a source of negative pressure.

In more particular example embodiments, the first manifold layer may comprise or consist of open-cell foam, and the second manifold layer may comprise or consist of felted open-cell foam.

In some example embodiments, the apparatus may comprise one or more additional layers. For example, the apparatus may include a layer adapted to inhibit tissue growth into the first manifold layer, such as a fenestrated polymer film. Additionally or alternatively, the apparatus may comprise a fixation layer, such as a layer of perforated silicone.

In some example embodiments, an apparatus may comprise a manifold layer and a cover layer coupled to the manifold layer. The manifold layer may have a first thickness and a first stiffness, and the cover layer may have a second thickness greater than the first thickness and a second stiffness greater than the first stiffness. A fluid interface may be configured to fluidly couple the manifold layer to a fluid conductor through the cover layer. In some examples, the cover layer may comprise closed-cell foam.

In some example embodiments, an apparatus according to this disclosure may be used to treat a tissue site with negative pressure, including treatment of soft tissue proximate to a tissue site. The tissue site may be a curved tissue site, such as a breast, a shoulder, an arm, a leg, a knee joint, or an ankle joint. The tissue site may include an incision in some examples.

In some example embodiments, a method of treating a tissue site may include applying a first manifold layer, a second manifold layer, and a cover layer over the tissue site; fluidly coupling a source of negative pressure to at least one of the first manifold layer and the second manifold layer through the cover layer; and applying negative pressure from the source of negative pressure to the second manifold layer; wherein the first manifold layer has a first thickness and a first stiffness, and the second manifold layer has a second thickness greater than the first thickness and a second stiffness greater than the first stiffness. The method of treatment may promote circulation through a subcutaneous lymph vascular network in some examples.

In some example embodiments, an apparatus for promoting circulation through a subcutaneous lymph vascular network may include a manifold layer and a support layer adjacent to the manifold layer. The manifold layer may have a first stiffness and the support layer may have a second stiffness greater than the first stiffness. A fluid interface may be configured to fluidly couple at least one of the manifold layer and the support layer to a fluid conductor.

In some example embodiments, an apparatus for promoting circulation through a subcutaneous lymph vascular network may include a manifold layer and a support layer adjacent to the manifold layer. The manifold layer may have a first stiffness from about 800 gram-force to about 1000 gram-force. The support layer may have a second stiffness from about 800 gram-force to about 3000 gram-force. A fluid interface may be configured to fluidly couple at least one of the manifold layer and the support layer to a fluid conductor.

In another example embodiment, a method of treating a tissue site may include applying a manifold layer, a support layer, and a cover over the tissue site; fluidly coupling a source of negative pressure to at least one of the manifold layer and the support layer through the cover layer; and applying negative pressure from the source of negative pressure to the manifold layer; wherein the manifold layer has a first thickness and a first stiffness, and the support layer has a second thickness and a second stiffness, the second thickness less than the first thickness. The method of treatment may promote circulation through a subcutaneous lymph vascular network in some examples.

In some example embodiments, a test model may include a body having a first end and a second end, a structural member extending through the body from the first end to the second end, and one or more channels extending through the body from the first end to the second end. The test model may be used to simulate circulation through a subcutaneous lymph vascular network.

Objectives, advantages, and a preferred mode of making and using the claimed subject matter may be understood best by reference to the accompanying drawings in conjunction with the following detailed description of illustrative example embodiments.

BRIEF DESCRIPTION OF THE DRAWINGS

FIG. 11 is a table of measurements taken during a test with the test model of FIG. 7;

FIG. 12 is a table of measurements taken during another test with the test model of FIG. 7;

FIG. 15 is a perspective view of the dressing of FIG. 13 as rolled to form a cuff or wrap around an appendage;

FIG. 18A and FIG. 18B are tables of material properties and performance data of example configurations of the dressing of FIG. 13 using the test setup of FIG. 16;

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

Figure 1:
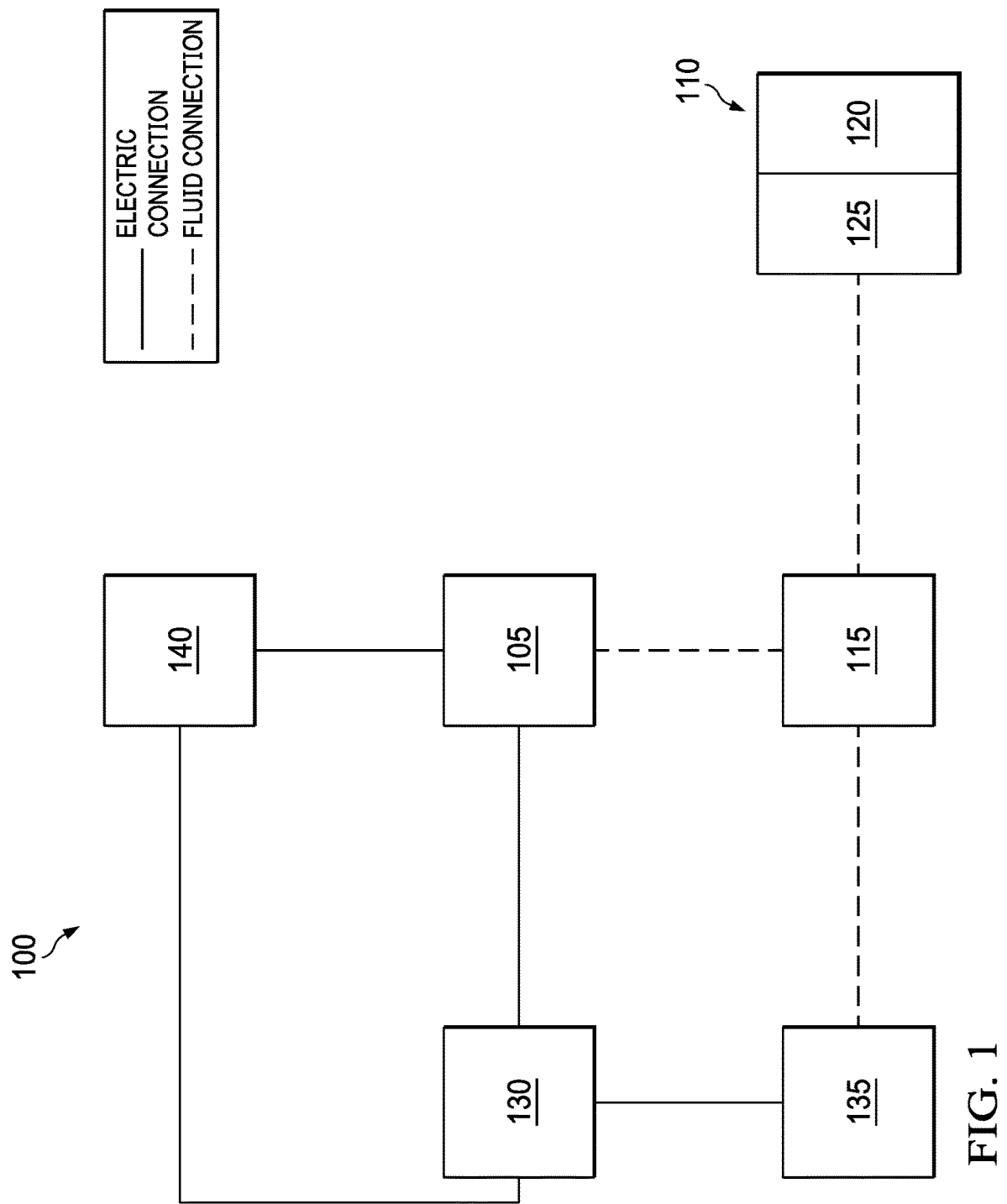
FIG. 1 is a block diagram of an example embodiment of a therapy system that can provide negative-pressure treatment in accordance with this specification.

FIG. 1 is a block diagram of an example embodiment of a therapy system 100 that can provide negative-pressure therapy to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Tex.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130 and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, may be any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITE-FOAM™ dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polyamide copolymers. Such materials are commercially available as, for example, Tegaderm® drape, commercially available from 3M Company, Minneapolis Minn.; polyurethane (PU) drape, commercially available from Avery Dennison Corporation, Pasadena, Calif.; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 g/m$^2$/24 hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" refers to a location in a fluid path relatively closer to a source of negative pressure or further away from a source of positive pressure. Conversely, the term "upstream" refers to a location further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

Figure 2:
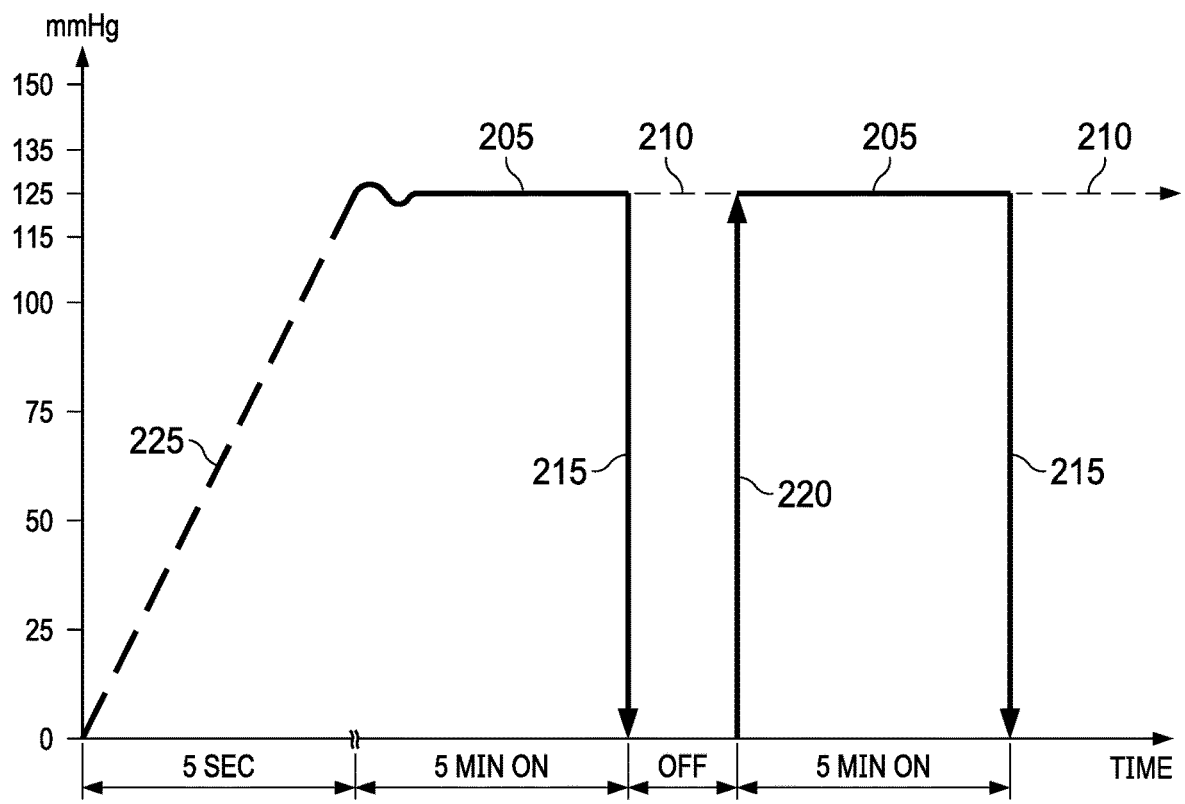
FIG. 2 is a graph illustrating additional details of example pressure control modes that may be associated with some embodiments of the therapy system of FIG. 1.

FIG. 2 is a graph illustrating additional details of an example control mode that may be associated with some embodiments of the controller 130. In some embodiments, the controller 130 may have a continuous pressure mode, in which the negative-pressure source 105 is operated to provide a constant target negative pressure, as indicated by line 205 and line 210, for the duration of treatment or until manually deactivated. Additionally or alternatively, the controller may have an intermittent pressure mode, as illustrated in the example of FIG. 2. In FIG. 2, the x-axis represents time and the y-axis represents negative pressure generated by the negative-pressure source 105 over time. In the example of FIG. 2, the controller 130 can operate the negative-pressure source 105 to cycle between a target pressure and atmospheric pressure. For example, the target pressure may be set at a value of 125 mmHg, as indicated by line 205, for a specified period of time (e.g., 5 min), followed by a specified period of time (e.g., 2 min) of deactivation, as indicated by the gap between the solid lines 215 and 220. The cycle can be repeated by activating the negative-pressure source 105, as indicated by line 220, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time, as indicated by the dashed line 225. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time, as indicated by the solid line 220, may be a value substantially equal to the initial rise time as indicated by the dashed line 225.

Figure 3:
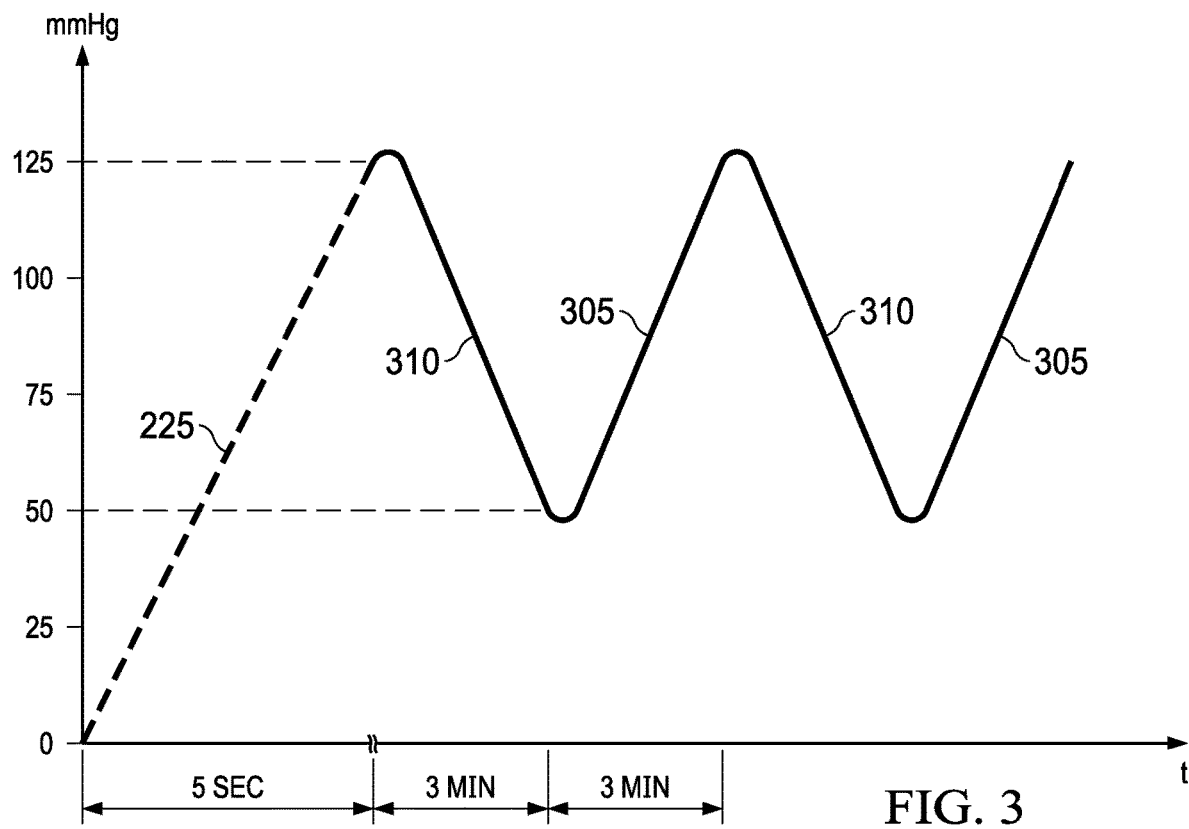
FIG. 3 is a graph illustrating additional details that may be associated with another example pressure control mode in some embodiments of the therapy system of FIG. 1.

FIG. 3 is a graph illustrating additional details that may be associated with another example pressure control mode in some embodiments of the therapy system 100. In FIG. 3, the x-axis represents time and the y-axis represents negative pressure generated by the negative-pressure source 105. The target pressure in the example of FIG. 3 can vary with time in a dynamic pressure mode. For example, the target pressure may vary in the form of a triangular waveform, varying between a negative pressure of 50 and 125 mmHg with a rise time 305 set at a rate of +25 mmHg/min. and a descent time 310 set at −25 mmHg/min. In other embodiments of the therapy system 100, the triangular waveform may vary between negative pressure of 25 and 125 mmHg with a rise time 305 set at a rate of +30 mmHg/min and a descent time 310 set at −30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 4:
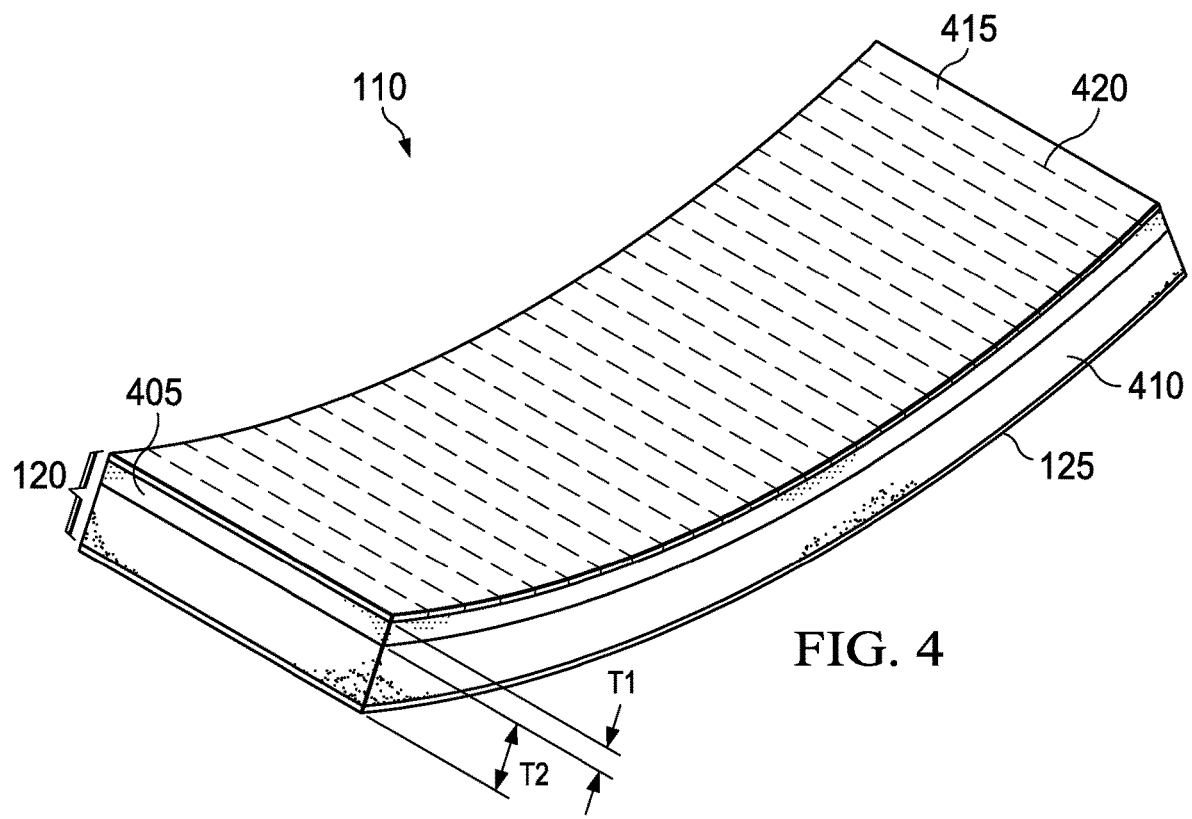
FIG. 4 is a perspective view of an example of a dressing that may be associated with some embodiments of the therapy system of FIG. 1.

FIG. 4 is a perspective view of an example of the dressing 110 of FIG. 1, illustrating additional details that may be associated with some embodiments. As illustrated in the example of FIG. 4, the tissue interface 120 may comprise more than one layer. In some examples, the tissue interface 120 may include an inner layer comprising or consisting essentially of a manifold. The tissue interface 120 may also include an outer layer comprising or consisting essentially of a manifold in some examples; in other examples, the outer layer may comprise or consist essentially of a medical-grade, closed-cell foam. In some examples, the inner layer may be configured to be positioned between the outer layer and the tissue site. In some examples, the inner layer may be proximate the tissue site and the outer layer may be distal to the tissue site. In some examples, the inner layer may be directly contacting the tissue site.

In the example of FIG. 4, the tissue interface 120 comprises a first manifold layer 405 and a second manifold layer 410, which may be curved in some embodiments. In some examples, the first manifold layer 405 may be the inner layer and the second manifold layer 410 may be the outer layer. In some examples, the first manifold layer 405, the second manifold layer 410, and the cover 125 may be disposed in a stacked relationship with the second manifold layer 410 interposed between the first manifold layer 405 and the cover 125. In some embodiments, the cover 125 may be omitted or the cover 125 may comprise a suitable closed-cell foam. For example, the cover 125 may not be necessary if the tissue interface 120 has an outer layer of suitable closed-cell foam. The second manifold layer 410 may be coupled to the first manifold layer 405, and the cover 125 may be coupled to the second manifold layer 410 in some embodiments. For example, the second manifold layer 410 may be disposed adjacent to the first manifold layer 405, and the cover 125 may be disposed adjacent to the second manifold layer 410. In some embodiments, the second manifold layer 410 may be laminated to the first manifold layer 405, and the cover 125 may be laminated to the second manifold layer 410.

In some examples, the outer layer may be stiffer than the inner layer. For example, the second manifold layer 410 may be stiffer than the first manifold layer 405. The stiffness of the second manifold layer 410 may be about four to about seven times greater than the stiffness of the first manifold layer 405 in some configurations. In some examples, the stiffness of the second manifold layer 410 may be about five times greater than the stiffness of the first manifold layer 405. In some examples, the stiffness of the first manifold layer 405 and the second manifold layer 410 may be tested using a Compression Load Deflection test. Using the Compression Load Deflection test, the force required to compress a sample of a material may be measured. The 25% Compression Load Deflection is the force required to compress a sample of a material by 25%. The 65% Compression Load Deflection is the force required to compress a sample of a material by 65%. In some examples, the first manifold layer 405 may have a stiffness in a range of about 0.3-0.4 pounds per square inch (25% Compression Load Deflection), and the second manifold layer 410 may have a stiffness in a range of about 1.5-2 pounds per square inch (25% Compression Load Deflection).

The first manifold layer 405 and the second manifold layer 410 may also have different thicknesses in some embodiments. As illustrated in FIG. 4, the second manifold layer 410 may be thicker than the first manifold layer 405. For example, the first manifold layer 405 may have a first thickness T1, the second manifold layer 410 may have a second thickness T2, and T2 may be greater than T1. In some configurations, the thickness T1 may be about 5 millimeters to about 7 millimeters, and T2 may be about 11 millimeters to about 13 millimeters. T2 may be about twice T1 in some embodiments. For example, the first manifold layer 405 may have a thickness of about 6 millimeters, and the second manifold layer 410 may have a thickness of about 12 millimeters.

In some embodiments, the first manifold layer 405 may comprise or consist essentially of reticulated foam having pore sizes and free volume or open void space that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the first manifold layer 405 may also vary according to needs of a prescribed therapy. The 25% Compression Load Deflection of the first manifold layer 405 may be at least 0.35 pounds per square inch, and the 65% Compression Load Deflection may be at least 0.43 pounds per square inch. In some embodiments, the tensile strength of the first manifold layer 405 may be at least 10 pounds per square inch. The first manifold layer 405 may have a tear strength of at least 2.5 pounds per inch. In some embodiments, the first manifold layer 405 may be foam comprised of polyols such as polyester or polyether, isocyanate such as toluene diisocyanate, and polymerization modifiers such as amines and tin compounds. In some examples, the first manifold layer 405 may be reticulated polyurethane foam, such as found in GRANUFOAM™ dressing or V.A.C. VERAFLO™ dressing, both available from Kinetic Concepts, Inc. of San Antonio, Tex.

The second manifold layer 410 may also comprise or consist essentially of a reticulated foam in some embodiments. For example, the second manifold layer 410 may comprise or consist essentially of the same material as the first manifold layer 405, and may be felted to increase the stiffness of the second manifold layer 410.

In some examples, the tissue interface 120 may additionally include a layer adapted to prevent granulation, which may be particularly advantageous if used over an incision site. In some examples, the layer may comprise a suitable fabric or fenestrated film. In the example of FIG. 4, the layer consists essentially of a film layer 415 having fenestrations 420. The film layer 415 may be disposed adjacent to the first manifold layer 405, and may be coupled to the first manifold layer 405 in some configurations. In some embodiments, the film layer 415 may substantially cover a face of the first manifold layer 405. The film layer 415 may comprise or consist essentially of a means for controlling or managing fluid flow, reducing or preventing tissue growth into the first manifold layer 405, or both. In some embodiments, the film layer 415 may comprise or consist essentially of a liquid-impermeable, elastomeric material. For example, the film layer 415 may comprise or consist essentially of a polymer film, such as a polyurethane film. In some embodiments, the film layer 415 may comprise or consist essentially of the same material as the cover 125. The film layer 415 may also have a smooth or matte surface texture in some embodiments. A glossy or shiny finish better or equal to a grade B3 according to the SPI (Society of the Plastics Industry) standards may be particularly advantageous for some applications. In some embodiments, variations in surface height may be limited to acceptable tolerances. For example, the surface of the film layer 415 may have a substantially flat surface, with height variations limited to 0.2 millimeters over a centimeter.

In some embodiments, the film layer 415 may be hydrophobic. The hydrophobicity of the film layer 415 may vary, but may have a contact angle with water of at least ninety degrees in some embodiments. In some embodiments, the film layer 415 may have a contact angle with water of no more than 150 degrees. For example, in some embodiments, the contact angle of the film layer 415 may be in a range of at least 90 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things. Non-limiting examples of such integrated systems may include the FTÅ125, FTÅ200, FTÅ2000, and FTÅ4000 systems, all commercially available from First Ten Angstroms, Inc., of Portsmouth, Va., and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles herein represent averages of 5-9 measured values, discarding both the highest and lowest measured values. The hydrophobicity of the film layer 415 may be further enhanced with a hydrophobic coating of other materials, such as silicones and fluorocarbons, either as coated from a liquid, or plasma coated.

The film layer 415 may also be suitable for welding to other layers, including the first manifold layer 405. For example, the film layer 415 may be adapted for welding to polyurethane foams using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene.

The area density of the film layer 415 may vary according to a prescribed therapy or application. In some embodiments, an area density of less than 40 grams per square meter may be suitable, and an area density of about 20-30 grams per square meter may be particularly advantageous for some applications.

In some embodiments, for example, the film layer 415 may comprise or consist essentially of a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styrenics, silicones, fluoropolymers, and acetates. A thickness between 20 microns and 100 microns may be suitable for many applications. Films may be clear, colored, or printed. More polar films suitable for laminating to a polyethylene film include polyamide, co-polyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

As illustrated in the example of FIG. 4, the fenestrations 420 can be distributed uniformly or randomly across the film layer 415. The fenestrations 420 may be bi-directional and pressure-responsive. For example, each of the fenestrations 420 generally may comprise or consist essentially of an elastic passage that is normally unstrained to substantially reduce liquid flow, and can expand or open in response to a pressure gradient. In some embodiments, the fenestrations 420 may comprise or consist essentially of perforations in the film layer 415. Perforations may be formed by removing material from the film layer 415. For example, perforations may be formed by cutting through the film layer 415, which may also deform the edges of the perforations in some embodiments. In the absence of a pressure gradient across the perforations, the passages may be sufficiently small to form a seal or fluid restriction, which can substantially reduce or prevent liquid flow. Additionally or alternatively, one or more of the fenestrations 420 may be an elastomeric valve that is normally closed when unstrained to substantially prevent liquid flow, and can open in response to a pressure gradient. A fenestration in the film layer 415 may be a suitable valve for some applications.

Figure 5:
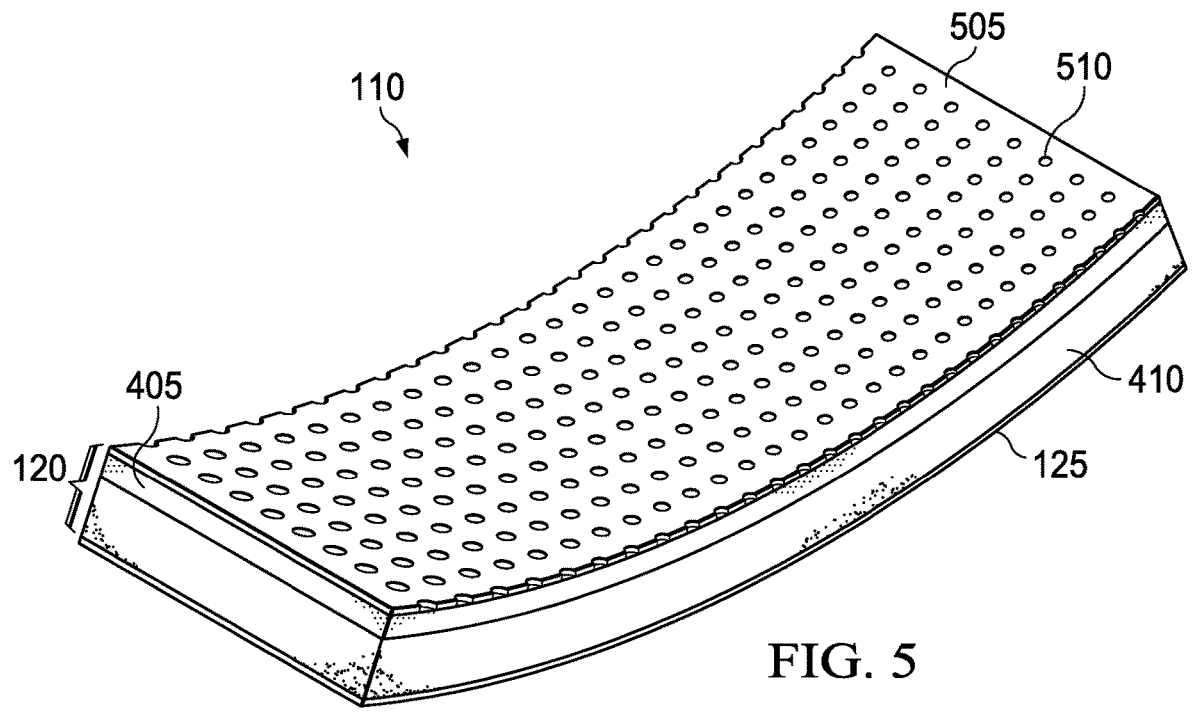
FIG. 5 is a perspective view of another example configuration of a dressing that may be associated with some embodiments of the therapy system of FIG. 1.

FIG. 5 is a perspective view of another example configuration of the dressing 110 of FIG. 1, illustrating additional details that may be associated with some embodiments. As illustrated in the example of FIG. 5, the tissue interface 120 may additionally or alternatively comprise a bonding layer 505. In some embodiments, the bonding layer 505 may substantially cover a face of the first manifold layer 405. The bonding layer 505 may be formed from a soft, tacky material, such as a suitable gel material, and may have a substantially flat surface. For example, the bonding layer 505 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive, polyurethane, polyolefin, or hydrogenated styrenic copolymers. In some embodiments, the bonding layer 505 may have a thickness between about 200 microns (μm) and about 1000 microns (μm). In some embodiments, the bonding layer 505 may have a hardness between about 5 Shore OO and about 80 Shore OO. Further, the bonding layer 505 may be comprised of hydrophobic or hydrophilic materials.

In some embodiments, the bonding layer 505 may be a hydrophobic-coated material. For example, the bonding layer 505 may be formed by coating a spaced material, such as, for example, woven, nonwoven, molded, or extruded mesh with a hydrophobic material. The hydrophobic material for the coating may be a soft silicone, for example.

The bonding layer 505 of FIG. 5 has apertures 510. The apertures 510 may be formed by cutting, perforating, or by application of local RF or ultrasonic energy, for example, or by other suitable techniques for forming an opening or perforation in the bonding layer 505. The apertures 510 may have a uniform distribution pattern, or may be randomly distributed in the bonding layer 505. The apertures 510 may have many shapes, including circles, squares, stars, ovals, polygons, slits, complex curves, rectilinear shapes, triangles, for example, or may have some combination of such shapes.

Each of the apertures 510 may have uniform or similar geometric properties. For example, in some embodiments, each of the apertures 510 may be circular apertures, having substantially the same diameter. In some embodiments, each of the apertures 510 may have a diameter of about 1 millimeter to about 50 millimeters. In other embodiments, the diameter of each of the apertures 510 may be about 1 millimeter to about 20 millimeters. In other embodiments, geometric properties of the apertures 510 may vary. For example, the diameter of the apertures 510 may vary depending on the position of the apertures 510 in the bonding layer 505.

In some examples, the bonding layer 505 may be used in combination with the film layer 415. For example, in some embodiments, the film layer 415 may be disposed between the first manifold layer 405 and the bonding layer 505, and at least some of the fenestrations 420 and the apertures 510 may be registered or aligned.

In some embodiments, one or more layers of the tissue interface 120 may be coextensive. For example, the second manifold layer 410 may be cut flush with the edge of the first manifold layer 405. The cover 125 may also be coextensive with the tissue interface 120, or may be larger to provide a margin for attaching to an attachment device.

The cover 125, the first manifold layer 405, the second manifold layer 410, the film layer 415, the bonding layer 505, or various combinations may be assembled before application or at the tissue site or location of treatment. In some embodiments, the dressing 110 may be provided as a single, composite dressing.

In use, the tissue interface 120 may be placed within, over, on, or otherwise proximate to a tissue site, such as an incision and adjacent epidermis. The film layer 415, the bonding layer 505, or both may be interposed between the first manifold layer 405 and a tissue site, which can substantially reduce or eliminate adverse interaction between the first manifold layer 405 and the tissue site. For example, the bonding layer 505 may be placed over an incision and undamaged epidermis to prevent direct contact with the first manifold layer 405. The bonding layer 505 may be sufficiently tacky to hold the dressing 110 in position, while also allowing the dressing 110 to be removed or re-positioned without trauma to the tissue site. In some examples, if the cover 125 provides a margin around the tissue interface 120, the cover 125 may be attached to the epidermis or other another attachment surface to seal the tissue interface 120. Additionally or alternatively, a secondary cover may be used to seal any exposed margin or joints around the tissue interface 120. The negative-pressure source 105 may be fluidly coupled to the tissue interface 120 through the cover 125. The dressing 110 may include or be coupled to a fluid interface configured to fluidly couple at least one of the first manifold layer 405 and the second manifold layer 410 to the negative-pressure source 105.

The geometry and dimensions of the tissue interface 120, the cover 125, or both may vary to suit a particular application or anatomy. For example, the geometry or dimensions of the tissue interface 120 and the cover 125 may be adapted to provide an effective and reliable seal against challenging anatomical surfaces, such as a breast, shoulder, elbow, or heel, at and around a tissue site. In some examples, the tissue interface 120 and the cover 125 may be configured to be applied to an appendage, such as an arm or leg, including joints such as a knee or ankle joint.

Figure 6A:
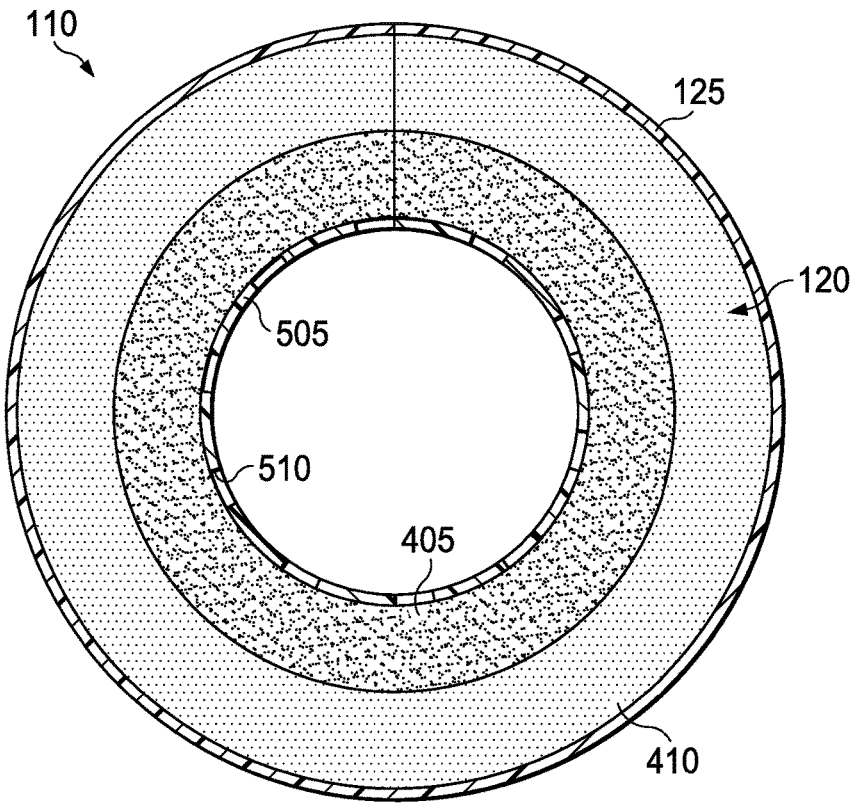
FIG. 6A and FIG. 6B are schematic sections of the dressing of FIG. 5 as rolled to form a cuff or wrap around an appendage.
Figure 6B:
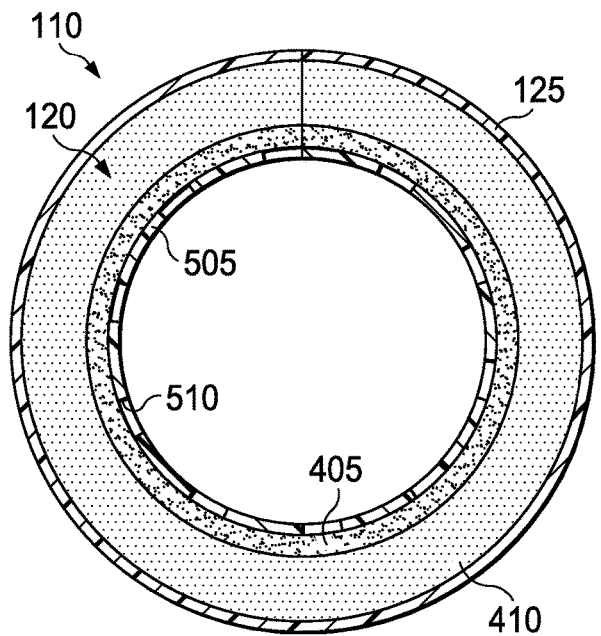

FIG. 6A and FIG. 6B are schematic sections of the dressing 110 of FIG. 5 as rolled to form at least a partial cuff or wrap around a curved tissue site, such as an appendage. FIG. 6A illustrates the dressing 110 without negative pressure applied, and FIG. 6B illustrates the dressing 110 with negative pressure applied. Negative pressure applied through the tissue interface 120 can create a compressive force on a tissue site. As illustrated in FIG. 6B, the lower stiffness of the first manifold layer 405 can allow the first manifold layer 405 to compress more than the second manifold layer 410, which can surprisingly increase perfusion through soft tissue around a tissue site.

For example, surprising results were demonstrated by testing an embodiment of the dressing 110 to measure flow rates through a test rig. Four test samples were wrapped around a test model configured to simulate an appendage with bone and soft tissue.

Figure 7:
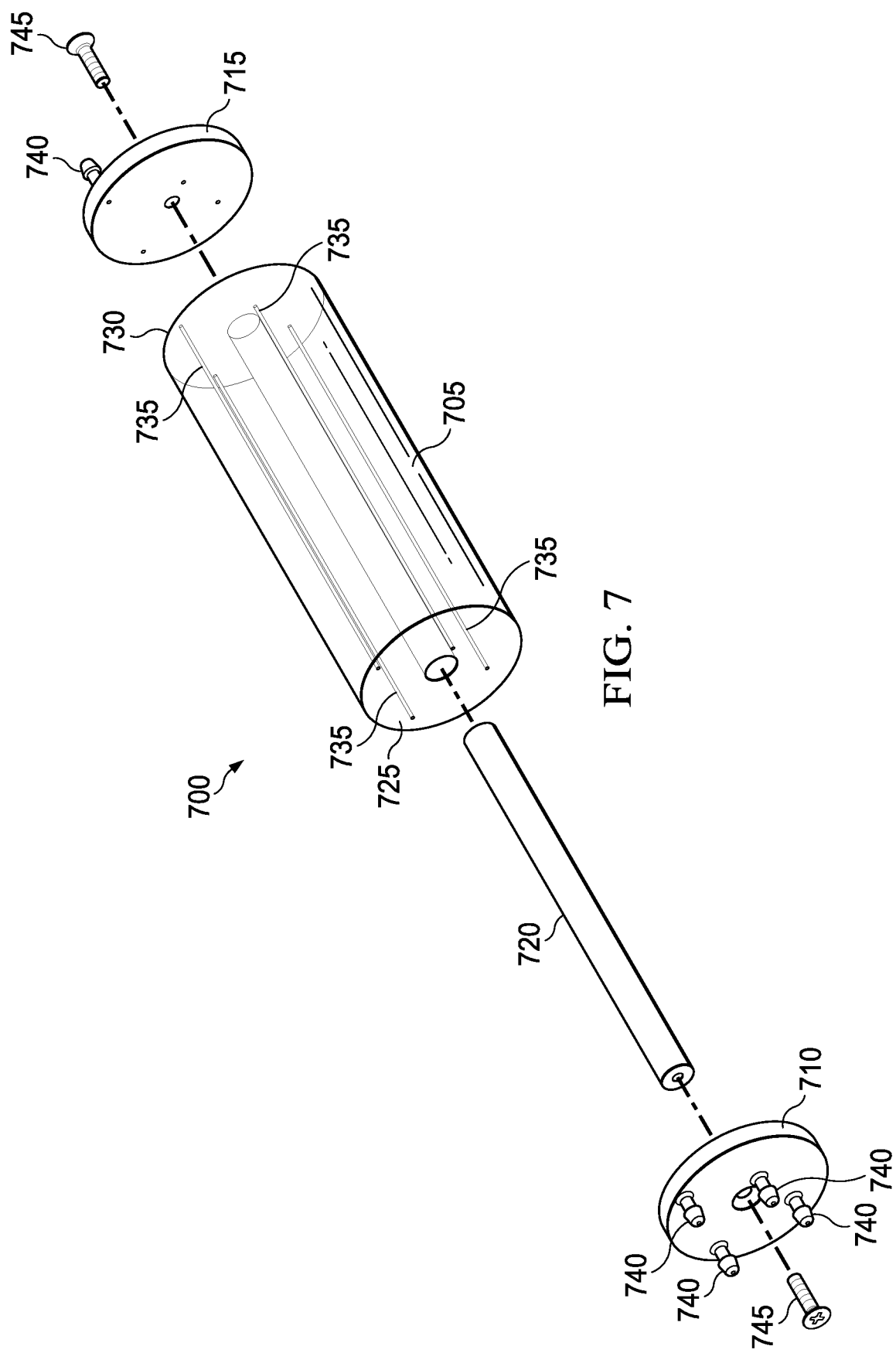
FIG. 7 is an exploded view of an example of a test model.

FIG. 7 is an isometric view of an embodiment of a test model 700. The test model 700 may include a body 705, a first end cap 710, a second end cap 715, and a structural member 720. The body 705 may have a first end 725 and a second end 730. In some embodiments, the body 705 may be cylindrically shaped and may have a diameter in a range of about 25 millimeters to about 160 millimeters. In some embodiments, the body 705 may have a diameter of about 50 millimeters. In some embodiments, the body 705 may have a length from the first end 725 to the second end 730 of about 75 millimeters to about 300 millimeters. In some embodiments, the body 705 may have a length from the first end 725 to the second end 730 of about 150 millimeters. In some embodiments, the body 705 may be constructed of a silicone material. The silicone material may be a soft silicone and may be made to look, feel, and move like living tissue. In some embodiments, the body 705 may be molded from PLATSIL™ Gel-10 having a Shore A hardness of 10+/−2 available from Polytek Development Corp.

The body 705 may have one or more channels 735 extending through the body 705 from the first end 725 to the second end 730. The channels 735 may be cast through the length of the body 705 to simulate a lymphatic network through an appendage. In some embodiments, each channel 735 in the population of channels 735 may have the same diameter. In some embodiments, the channels 735 may have different diameters. In some embodiments, the population of channels 735 may have a diameter in a range of about 0.75 millimeters to about 2.0 millimeters. In some embodiments, the population of channels 735 may have a diameter of about 1.6 millimeters.

The structural member 720 may extend through the body 705 from the first end 725 to the second end 730. In some embodiments, the structural member 720 may be a cylindrical rod having a diameter of about 10 millimeters. In some embodiments, the structural member 720 may be a cylindrical rod having a diameter in a range of about 5 millimeters to about 30 millimeters. The structural member 720 may be a rigid shaft formed of, for example, steel, stainless steel, aluminum, titanium, or other suitable metals or alloys. In some embodiments, the structural member 720 may be a rigid shaft formed of polyvinyl chloride (PVC), polypropylene (PP), polycarbonate (PC), acrylic (PMMA), acetal (polyoxymethylene (POM)), acrylonitrile butadiene styrene (ABS), or other suitably rigid plastics. In some embodiments, the body 705 is molded around the structural member 720. The structural member 720 may be located through the center of the body 705. In some embodiments, the structural member 720 may be offset from the center of the body 705. The structural member 720 may simulate a bone supporting tissue.

The first end cap 710 may be coupled to the first end 725 of the body 705 and the second end cap 715 may be coupled to the second end 730 of the body 705. The first end cap 710 and the second end cap 715 may each comprise one or more fittings 740 extending from the first end cap 710 and the second end cap 715. Each fitting 740 may be fluidly coupled with a channel 735 extending through the body 705. The number of fittings 740 in each of the first end cap 710 and the second end cap 715 may equal the number of channels 735 in the body 705. As shown in FIG. 7, the fittings 740 may be barbed fittings. In some embodiments, the fittings 740 may be threaded fittings. The fittings 740 are configured to couple the test model 700 to flexible tubing.

The first end cap 710 and the second end cap 715 may be formed of, for example, steel, stainless steel, aluminum, titanium, or other suitable metals or alloys. In some embodiments, the first end cap 710 and the second end cap 715 may be formed of polyvinyl chloride (PVC), polypropylene (PP), polycarbonate (PC), acrylic (PMMA), acetal (polyoxymethylene (POM)), acrylonitrile butadiene styrene (ABS), or other suitably rigid plastics. The first end cap 710 and the second end cap 715 may be manufactured in a variety of ways, including, but not limited to, 3D printing, injection molding, machining, and casting.

In some embodiments, the body 705 may be molded around at least a portion of the first end cap 710 and/or the second end cap 715. The first end cap 710 and the second end cap 715 may be coupled to the structural member 720. In some embodiments, the first end cap 710 and the second end cap 715 may be coupled to the structural member 720 by screws 745. In some embodiments, the first end cap 710 and the second end cap 715 may be coupled to the structural member 720 by adhesives. In some embodiments, the first end cap 710 and the second end cap 715 may be coupled to the structural member 720 by welds. In some embodiments, the first end cap 710, the second end cap 715, and the structural member 720 may be integrally formed.

In some embodiments, the test model 700 may include a soft transition between the first end cap 710 and the body 705 and the second end cap 715 and the body 705. The soft transition may reduce the risk of shearing at the junction between the first end cap 710 and the body 705 and the second end cap 715 and the body 705. The soft transition, for example, may be provided by a short length of silicone tube to enable a flexible transition between the population of fittings 740 and the population of channels 735.

Figure 8:
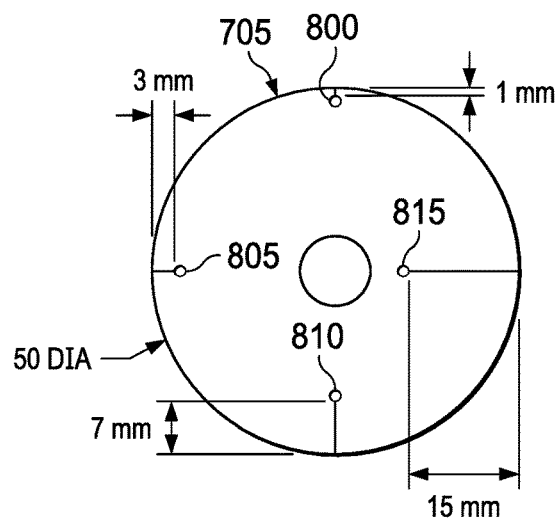
FIG. 8 is an end view of an example of a body of the test model of FIG. 7.

FIG. 8 is an end view of the body 705 illustrating additional details of an embodiment of the test model 700. As shown in FIG. 8, in some embodiments, the population of channels 735 may include a first channel 800 at a depth of 1 millimeter from the surface of the body 705, a second channel 805 at a depth of 3 millimeters from the surface of the body 705, a third channel 810 at a depth of 7 millimeters from the surface of the body 705, and a fourth channel 815 from the surface of the body 705 at a depth of 15 millimeters. In some embodiments, the body 705 may include more than four channels.

Figure 9:
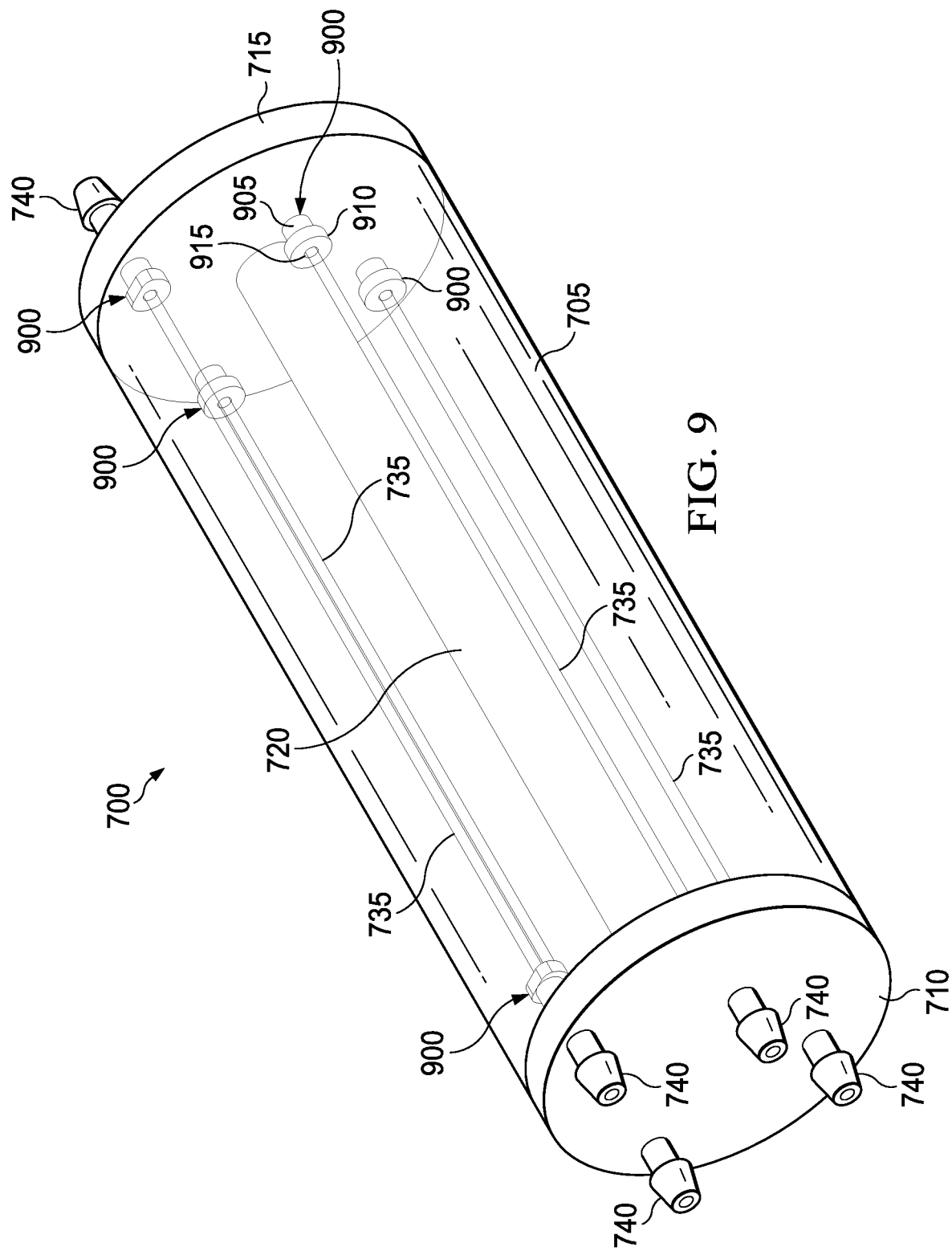
FIG. 9 is a perspective view of another example of a test model.

FIG. 9 is an isometric view illustrating another embodiment of the test model 700. As shown in FIG. 9, in some embodiments, the first end cap 710 and the second end cap 715 may each comprise one or more protrusions 900 extending from the first end cap 710 and the second end cap 715 away from the fittings 740. Each protrusion 900 may include a cylinder 905 with a head 910 at the end of the cylinder 905. The head 910 may have a larger diameter than the cylinder 905. In some embodiments, the protrusions 900 may be a barbed fitting. Each protrusion 900 may further include a channel 915 that is fluidly coupled with a channel 735 in the body 705 and a fitting 740. The protrusions 900 may be configured to engage with the body 705 to align the fittings 740 with the channels 735. The protrusions 900 may also aid in stabilizing the body 705. In some embodiments, the first end cap 710 and the second end cap 715 each include one protrusion 900. In some embodiments, the first end cap 710 and the second end cap 715 each include more than one protrusion 900. In some embodiments, the number of protrusions 900 in each of the first end cap 710 and the second end cap 715 may equal the number of channels 735 in the body 705.

Figure 10:
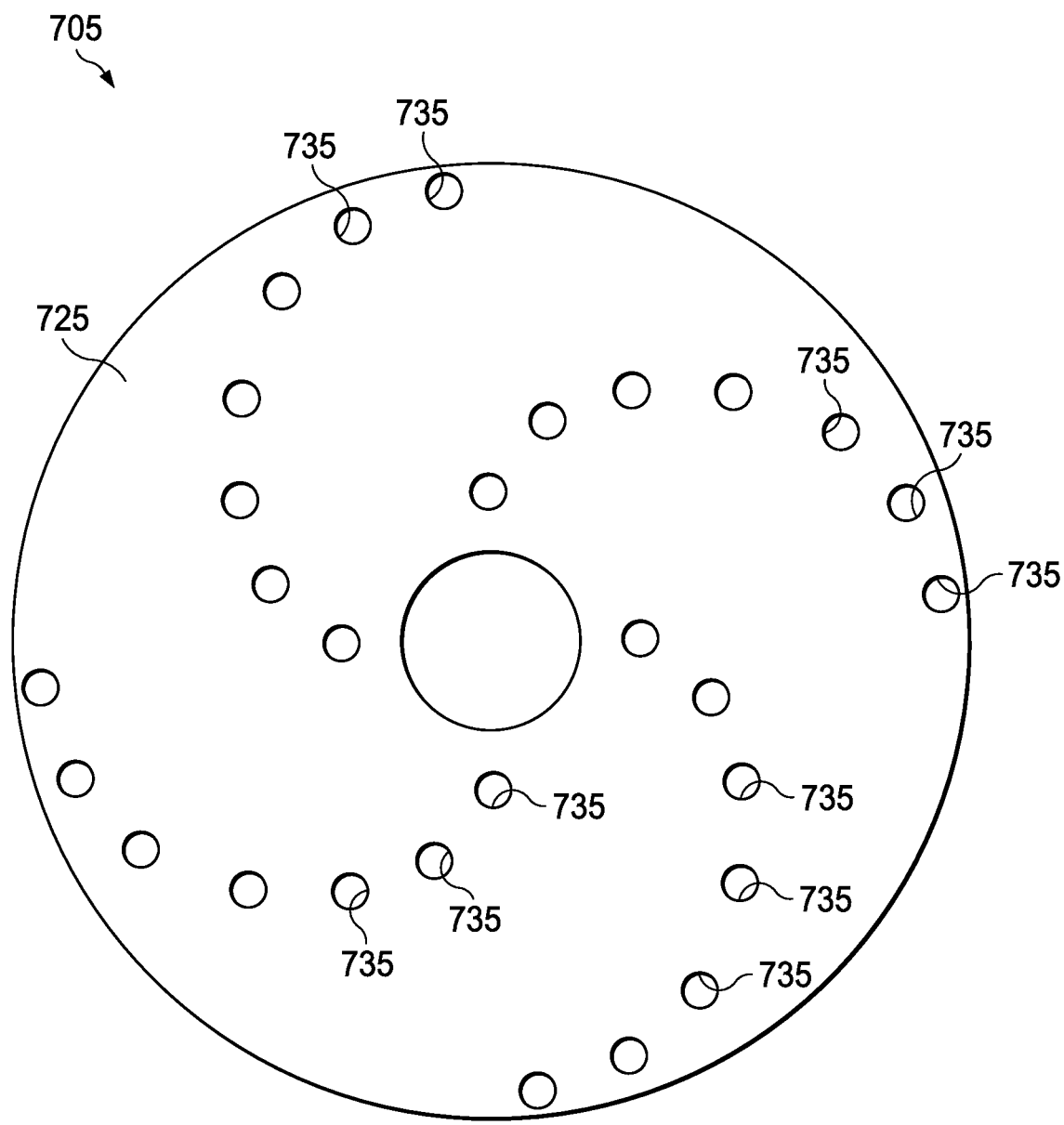
FIG. 10 is an end view of another example of a body of a test model.

FIG. 10 is an end view of the body 705 illustrating additional details of an embodiment of the test model 700. As shown in FIG. 10, the channels 735 may be arranged in a spiral pattern when viewed from the first end 725 or the second end 730 (not shown). The test model 700 may be scaled to represent a larger anatomy, such as for example, a human or animal arm, leg, thigh, or torso. For example, the test model 700 may have a diameter of about 160 millimeters and a length of about 290 millimeters.

During testing of samples of the dressing 110, the channels 735 were connected to an air supply with pressure set to a constant rate of 2 centimeters Hg. Measurements of air flow were taken with the sample dressings applied before and after negative pressure for individual channels 735 and all channels 735 combined.

FIG. 11 is a table of measurements taken during a first test, where Sample 1 is illustrative of a dressing having features analogous or similar to the example of FIG. 5, including an inner manifold layer and a stiffer outer manifold layer. More specifically, Sample 1 was constructed with an inner layer of reticulated foam and an outer layer of the reticulated foam that was felted to increase stiffness. Samples 2-4 comprised various conventional dressing configurations having manifold features without differential stiffness. FIG. 11 summarizes the results of the test, which surprisingly show increased performance with a stiffer outer layer of Sample 1. The data of FIG. 11 illustrate an increase in flow rate, on a percentage basis, through the channels 735 of the test model 700 with the application of negative pressure as compared to no negative pressure applied. The asterisk in FIG. 11 indicates that the measured flow rates were outside the range of the measurement device.

FIG. 12 summarizes results of a second test, in which Sample 1 was tested at different pressure levels. The results surprisingly demonstrate that flow rates increased with lower levels of negative pressure. That is, the flow rate through the channels 735 of the test model 700 was higher when the negative pressure applied to the Sample 1 was −100 mmHg as compared to −200 mmHg.

Figure 13:
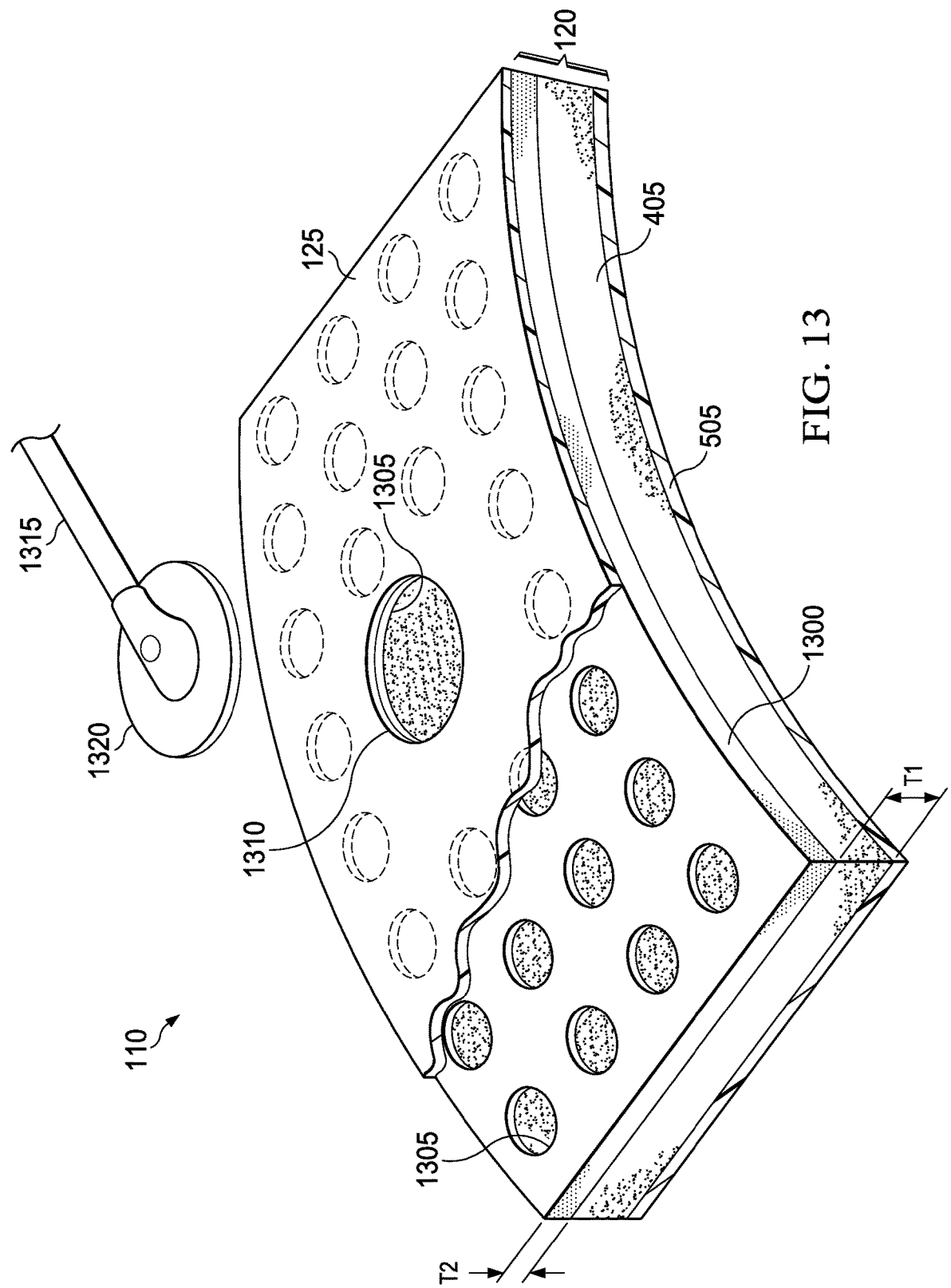
FIG. 13 is a perspective view of another example configuration of a dressing that may be associated with some embodiments of the therapy system of FIG. 1.

FIG. 13 is a perspective view of another example configuration of the dressing 110 of FIG. 1, illustrating additional details that may be associated with some embodiments. The tissue interface 120 of the dressing 110 may comprise the first manifold layer 405, an outer layer, such as a support layer 1300, and the cover 125. In some examples, the first manifold layer 405, the support layer 1300, and the cover 125 may be disposed in a stacked relationship with the support layer 1300 interposed between the first manifold layer 405 and the cover 125. In some embodiments, the cover 125 may be omitted. For example, the cover 125 may not be necessary if the support layer 1300 comprises a material that can provide a fluid seal, such as for example, a suitable closed-cell foam. The support layer 1300 may be coupled to the first manifold layer 405, and the cover 125 may be coupled to the support layer 1300 in some embodiments. For example, the support layer 1300 may be disposed adjacent to the first manifold layer 405, and the cover 125 may be disposed adjacent to the support layer 1300. In some embodiments, the support layer 1300 may be laminated to the first manifold layer 405, and the cover 125 may be laminated to the support layer 1300.

In some embodiments, the stiffness of the first manifold layer 405 and the support layer 1300 may be measured using ASTM D6828-02 Standard Test Method for Stiffness of Fabric by Blade/Slot Procedure. In some embodiments, the first manifold layer 405 may have a stiffness in a range of about 800 gram-force (gf) to about 1000 gram-force. In some embodiments, the first manifold layer 405 may have a stiffness of about 910 gram-force. In some embodiments, the support layer 1300 may have a stiffness in a range of about 500 gram-force to about 3000 gram-force. In some embodiments, the support layer 1300 may have a stiffness in a range of about 800 gram-force to about 2000 gram-force. In some embodiments, the support layer 1300 may have a stiffness in a range of about 1000 gram-force to about 2000 gram-force. In some embodiments, the support layer 1300 may have a stiffness in a range of about 1200 gram-force to about 1500 gram-force. In some embodiments, the support layer 1300 may have a stiffness equal to or greater than about 500 gram-force. In some embodiments, the support layer 1300 may have a stiffness equal to or greater than about 800 gram-force. In some embodiments, the support layer 1300 may have a stiffness equal to or greater than about 1000 gram-force. In some embodiments, the support layer 1300 may have a stiffness equal to or greater than about 1200 gram-force. In some embodiments, the support layer 1300 may have a stiffness equal to or greater than about 1400 gram-force. In some embodiments, the support layer 1300 may have a stiffness of about 725 gram-force. In some embodiments, the support layer 1300 may have a stiffness of about 834.75 gram-force. In some embodiments, the support layer 1300 may have a stiffness of about 846 gram-force. In some embodiments, the support layer 1300 may have a stiffness of about 1220 gram-force. In some embodiments, the support layer 1300 may have a stiffness of about 1446 gram-force. In some embodiments, the support layer 1300 may have a stiffness of about 1490 gram-force. In some embodiments, the support layer 1300 may have a stiffness of about 2326 gram-force. In some embodiments, the support layer 1300 may have a stiffness of about 11486 gram-force.

In some examples, the support layer 1300 may be stiffer than the first manifold layer 405. The stiffness of the support layer 1300 may be about 1.3 to about 13 times greater than the stiffness of the first manifold layer 405 in some configurations. In some embodiments, the support layer 1300 may be about 1.3 to about 2.6 times greater than the stiffness of the first manifold layer 405. In some embodiments, the support layer 1300 may be about 1.3 to about 1.7 times greater than the stiffness of the first manifold layer 405. In some embodiments, the support layer 1300 may be about 1.3 to about 1.6 times greater than the stiffness of the first manifold layer 405. In some embodiments, the support layer 1300 may be about 1.6 times greater than the stiffness of the first manifold layer 405.

The first manifold layer 405 and the support layer 1300 may also have different thicknesses in some embodiments. In some embodiments, the support layer 1300 may be thinner than the first manifold layer 405. For example, the first manifold layer 405 may have a first thickness T1, the support layer 1300 may have a second thickness T2, and T2 may be less than T1. In some configurations, the thickness T1 may be about 5 millimeters to about 7 millimeters, and T2 may be about 0.1 millimeters to about 3 millimeters. In some embodiments, the first manifold layer 405 may have a thickness of about 6.35 millimeters, and the support layer 1300 may have a thickness of about 1.96 millimeters.

In some embodiments, the support layer 1300 may comprise or consist essentially of a closed cell foam. For example, the support layer 1300 may comprise or consist essentially of a neoprene foam. In some embodiments, the support layer 1300 may comprise or consist essentially of a knit fabric. For example, the support layer 1300 may comprise or consist essentially of a double knit polyester fabric. For example, the support layer 1300 may comprise or consist essentially of a pique knit polyester fabric. For example, the support layer 1300 may comprise or consist essentially of a jersey knit blend of about 21% polyester, about 65% nylon, and about 14% spandex. In some embodiments, the support layer 1300 may comprise or consist essentially of a woven fabric. For example, the support layer 1300 may comprise or consist essentially of a 1×1 plain weave blend of about 65% polyester and about 35% cotton. For example, the support layer 1300 may comprise or consist essentially of a 3×1 twill weave blend of about 65% polyester and about 35% cotton. For example, the support layer 1300 may comprise or consist essentially of a 1×1 plain weave of polyester coated with polyurethane. In some embodiments, the support layer 1300 may comprise or consist essentially of a film. For example, the support layer 1300 may comprise or consist essentially of an 8 gauge polyvinyl chloride film. For example, the support layer 1300 may comprise or consist essentially of a 16 gauge polyvinyl chloride film. For example, the support layer 1300 may comprise or consist essentially of a 20 gauge polyvinyl chloride film. In some embodiments, the polyvinyl chloride film may be clear, transparent, or opaque. In some embodiments, the support layer 1300 may comprise or consist essentially of a composite film. For example, the support layer 1300 may comprise or consist essentially of a glass fabric coated with polytetrafluoroethylene (PTFE) resin. In some embodiments, the support layer 1300 may comprise or consist essentially of a mesh. For example, the support layer 1300 may comprise or consist essentially of a polyurethane foam grid mesh having a square grid. For example, the support layer 1300 may comprise or consist essentially of a multifilament nylon PA66 mesh having a square grid. For example, the support layer 1300 may comprise or consist essentially of a resorcinol formaldehyde latex coated glass mesh having a square grid. In some embodiments, the support layer 1300 may comprise or consist essentially of a non-woven material. For example, the support layer 1300 may comprise or consist essentially of a non-woven polyester fabric. For example, the support layer 1300 may comprise or consist essentially of a non-woven polyester fabric that has been heat pressed for one minute at about 375 degrees Fahrenheit. In some embodiments, the support layer 1300 may comprise or consist essentially of a rubber. For example, the support layer 1300 may comprise or consist essentially of acrylonitrile butadiene rubber.

As further shown in the example of FIG. 13, in some embodiments, the support layer 1300 may have one or more apertures 1305. The apertures 1305 may be formed by cutting, perforating, or by application of local RF or ultrasonic energy, for example, or by other suitable techniques for forming an opening or perforation in the support layer 1300. The apertures 1305 may have a uniform distribution pattern, or may be randomly distributed in the support layer 1300. In some embodiments, the apertures 1305 may be arrayed across the support layer 1300 with the apertures 1305 having staggered centers. For example, the apertures 1305 may be arrayed in a triangular pitch. In some embodiments, the apertures 1305 may be arrayed across the support layer 1300 with the apertures 1305 having straight centers. For example, the apertures 1305 may be arrayed in a rectangular pitch. The apertures 1305 may have many shapes, including circles, squares, stars, ovals, polygons, slits, complex curves, rectilinear shapes, triangles, for example, or may have some combination of such shapes. Each of the apertures 1305 may have uniform or similar geometric properties. For example, in some embodiments, each of the apertures 1305 may be circular apertures, having substantially the same diameter. In some embodiments, the apertures 1305 may be circles having a diameter in a range from about 1 millimeter to about 15 millimeters. In some embodiments, the apertures 1305 may be circles having a diameter in a range from about 5 millimeter to about 10 millimeters. In some embodiments, the apertures 1305 may be circles having a diameter of about 6.35 millimeters. In other embodiments, geometric properties of the apertures 1305 may vary. For example, the diameter of the apertures 1305 may vary depending on the position of the apertures 1305 in the support layer 1300.

In some embodiments, the apertures 1305 may be arrayed across the support layer 1300 with a center-to-center distance, or pitch, in a range from about 3 millimeters to about 50 millimeters. In some embodiments, the apertures 1305 may be arrayed across the support layer 1300 with a center-to-center distance, or pitch, of about 12.7 millimeters. In some embodiments, the apertures 1305 may be arrayed across the support layer 1300 with a center-to-center distance, or pitch, of about 25.4 millimeters. The apertures 1305 in the support layer 1300 result in an open area in the support layer 1300. The open area is a ratio of the total area of all the apertures 1300 to the total area of the support layer 1300. The open area may be expressed as a percentage. For example, for an open area of 25%, 25% of the area of the support layer 1300 is open and 75% of the area of the support layer 1300 is closed. In some embodiments, the open area may be in a range from about 3% to about 50%. In some embodiments, the open area may be in a range from about 4% to about 6%. In some embodiments, the open area may be in a range from about 10% to about 30%. In some embodiments, the open area may be less than 50%. In some embodiments, the open area may be about 4.9%. In some embodiments, the open area may be about 5.7%.

One of the apertures 1305 in the support layer 1300 may be fluidly coupled with an aperture 1310 in the cover 125 and may have a larger size to accommodate the size of the aperture 1310 in the cover 125. The dressing 110 may be coupled to the negative-pressure source 105 by a fluid conductor 1315 and a dressing interface 1320. The fluid conductor 1315 may be a flexible tube, which can be fluidly coupled on one end to the dressing interface 1320. The dressing interface 1320 may be an elbow connector, as shown in the example of FIG. 13, which can be placed over the aperture 1310 in the cover 125 and one or more of the apertures 1305 to provide a fluid path between the fluid conductor 1315 and the tissue interface 120. The one or more apertures 1305 may allow for negative pressure to be supplied to the first manifold layer 405 through the support layer 1300.

As shown in FIG. 13, in some embodiments, the dressing 110 may include the bonding layer 505. Additionally or alternatively, the dressing 110 may include the film layer 415 (not shown in FIG. 13) disposed between the first manifold layer 405 and the bonding layer 505.

Figure 14A:
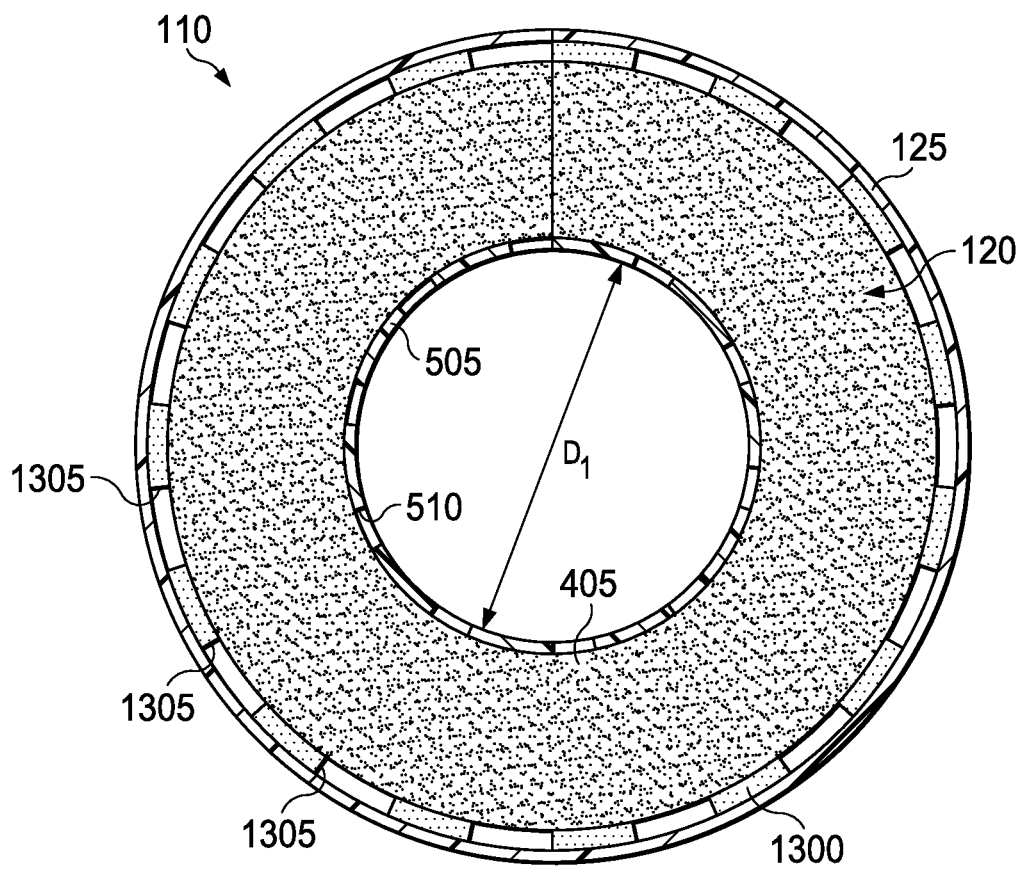
FIG. 14A and FIG. 14B are schematic sections of the dressing of FIG. 13 as rolled to form a cuff or wrap around an appendage.
Figure 14B:
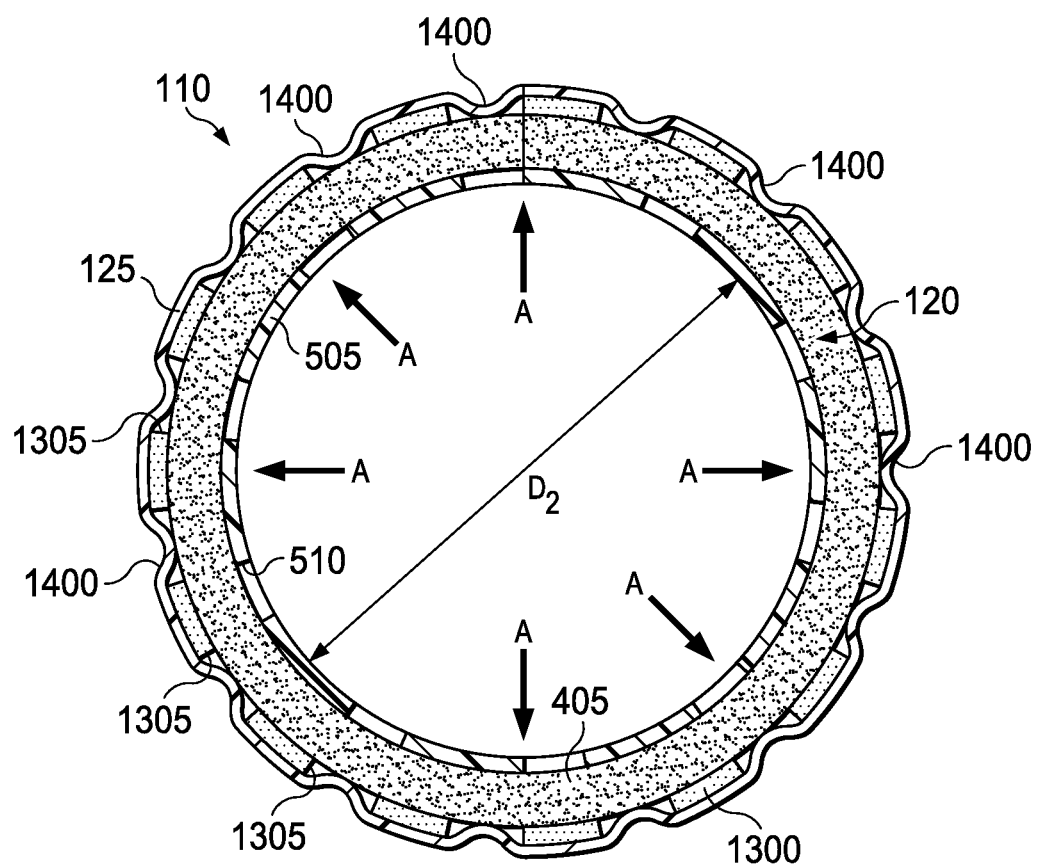

FIG. 14A and FIG. 14B are schematic sections of the dressing 110 of FIG. 13 as rolled to form at least a partial cuff or wrap around a curved tissue site, such as an appendage. FIG. 14A illustrates the dressing 110 without negative pressure applied, and FIG. 14B illustrates the dressing 110 with negative pressure applied. The test model 700 is not shown for clarity purposes. Without negative pressure applied, the dressing 110 may have a first inner dimension, such as, for example, a first inner diameter ($D_1$). With negative pressure applied, the dressing 110 may have a second inner dimension, such as, for example, a second inner diameter ($D_2$), wherein the second inner dimension is larger than the first inner dimension, such as, for example, $D_2 > D_1$. The increased second inner diameter ($D_2$) is shown in exaggerated form for illustrative purposes. Negative pressure applied through the tissue interface 120 can create an expansion force on a tissue site. As illustrated in FIG. 14B, the increased stiffness of the support layer 1300 allows for the first manifold layer 405 to collapse outwards under the application negative pressure to the tissue interface 120 leading to decompression of the underlying tissue and increased lymphatic flow. The outward collapse of the first manifold layer 405 (as shown by arrows A in FIG. 14B) pulls outward on the epidermis and underlying tissue, opening up the blood vessels and lymphatic pathways, which allows for a higher rate of perfusion through the blood vessels and lymphatic pathways. Thus, the increased outward pulling force can increase the diameter of the blood vessels and/or the lymphatic pathways which may increase the blood and lymphatic flow through the tissue site. The outward collapse of the first manifold layer 405 under the application of negative pressure can surprisingly increase perfusion through soft tissue around a tissue site. In some embodiments, for example, the dressing 110 can increase simulated lymphatic flow up to five times more than without the dressing 110.

Additionally, as shown in FIG. 14B, when negative pressure is applied to the dressing 110, portions of the cover 125 may be drawn into the apertures 1305 in the support layer 1300 toward the first manifold layer 405 forming indentations 1400.

FIG. 15 is an isometric view of the dressing 110 of FIG. 6 shown under the application of negative pressure. As shown in FIG. 15, the outline of the apertures 1305 may be visible through the cover 125 under the application of negative pressure. Additionally, the indentations 1400 formed by the cover 125 being drawn into the apertures 1305 may be visible and may be felt. The appearance of the outline of the apertures through the cover 125 under the application of negative pressure may be useful as an indicia that negative pressure is being applied to the tissue interface 120. If the outline of the support layer 1300 cannot be identified through the cover 125 after a certain length of time that negative pressure has been applied to the dressing 110, it may be an indication of a leak in the dressing 110.

Surprising results were demonstrated by testing embodiments of the dressing 110 shown in FIG. 13 to measure flow rates through the test model 700. Twenty test samples were wrapped around the test model 700.

Figure 16:
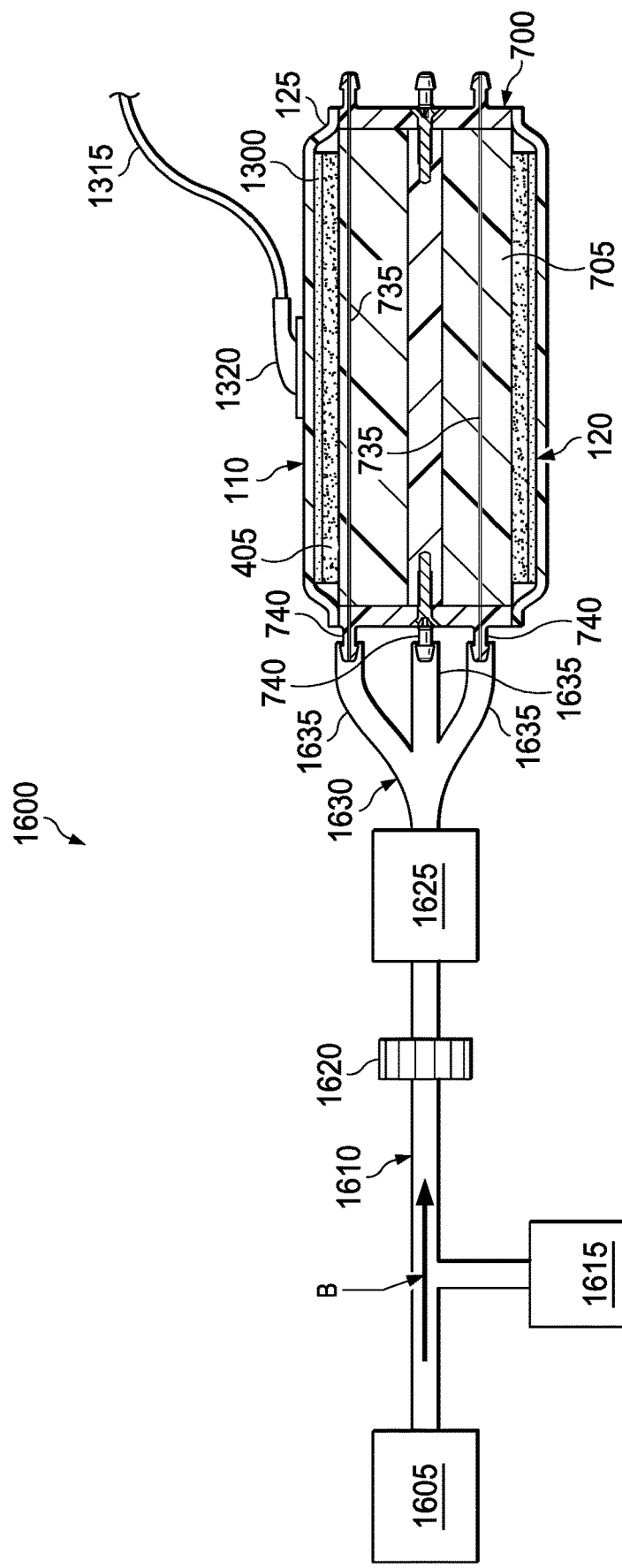
FIG. 16 is a schematic view of an example of a test setup for testing example configurations of the dressing of FIG. 13 using the test model of FIG. 7.

FIG. 16 is a schematic view of a test setup 1600 for measuring flow rates through the test model 700 using different embodiments of the dressing 110 shown in FIG. 13. As shown in FIG. 16, the test setup 1600 includes an air supply 1605, a fluid conductor 1610, a manometer 1615, a filter 1620, an air flow meter 1625, and a manifold 1630 coupled to the test model 700. The fluid conductor 1610 is fluidly coupled to the air supply 1605. The air supply 1605 may supply air to the test model 700 through the fluid conductor 1610 as shown by arrow B. The manometer 1615 may be fluidly coupled to the fluid conductor 1610 downstream of the air supply 1605. The manometer 1615 may be used to measure the pressure of the air in the fluid conductor 1610. The filter 1620 may be fluidly coupled in-line with the fluid conductor 1610 downstream of the manometer 1615. The filter 1620 may be used to filter the air before it enters the air flow meter 1625 and the test model 700. The air flow meter 1625 may be fluidly coupled in-line with the fluid conductor 1610 downstream of the filter 1620. The air flow meter 1625 may be used to measure the air flow rate through the test model 700. The manifold 1630 may be fluidly coupled in-line with the air flow meter 1625. The manifold 1630 may include a number of fluid conductors 1635 as the number of channels 735 of the test model 700. The fluid conductors 1635 of the manifold 1630 may be fluidly coupled to the fittings 740 of the test model 700.

Figure 17:
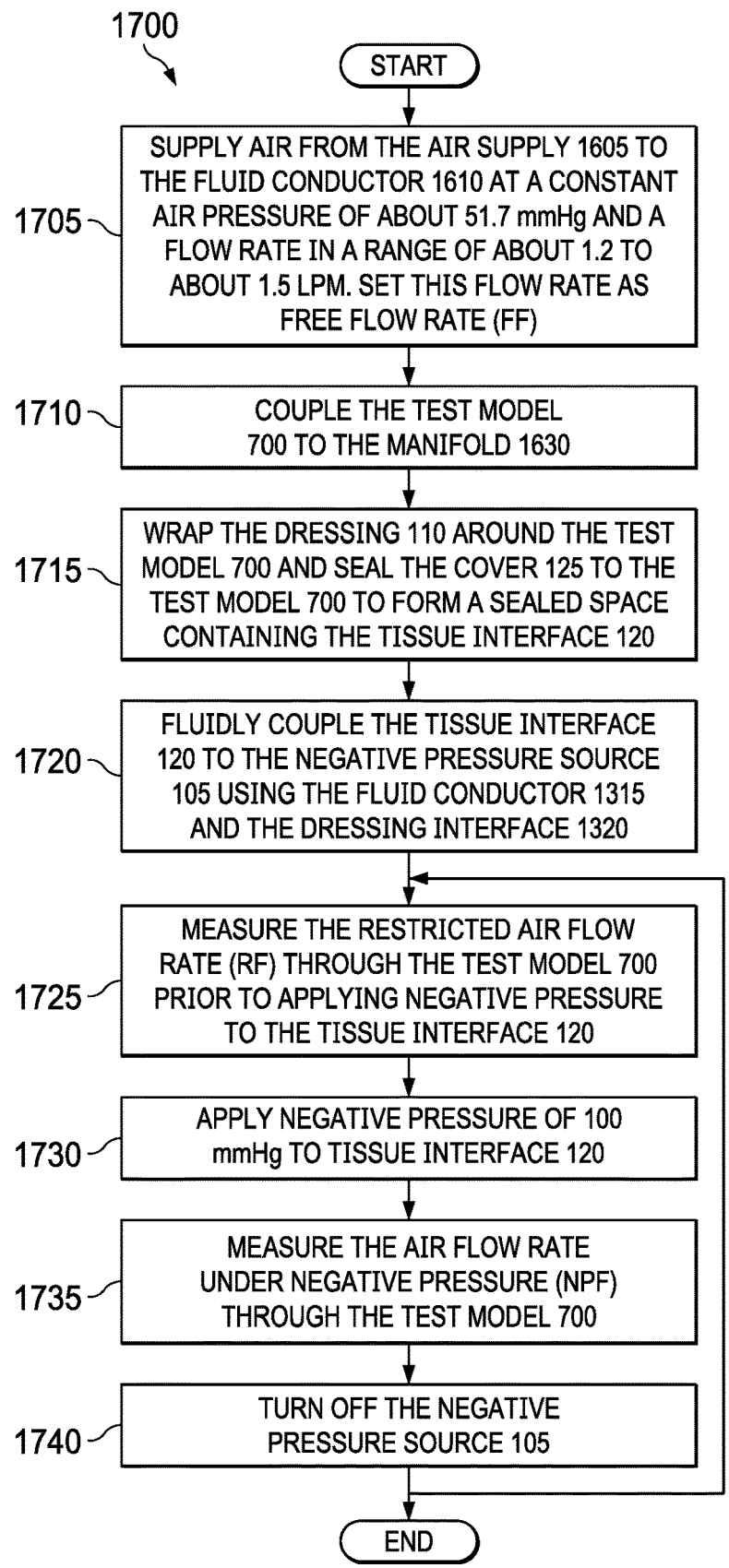
FIG. 17 is a flow chart illustrating a method of testing example configurations of the dressing of FIG. 13 using the test setup of FIG. 16.

FIG. 17 illustrates a method 1700 of testing embodiments of the dressing 110 shown in FIG. 13 using the test setup 1600 of FIG. 16. At step 1705, the air supply 1605 is turned on and regulated to provide a constant air pressure of about 51.7 mmHg (about 1 psi) at a flow rate in a range of about 1.2 liters per minute (1 pm) to about 1.5 liters per minute (1 pm). This flow rate is set as the free flow rate (FF). At step 1710, the test model 700 is coupled to the manifold 1630 such that the fluid conductors 1635 of the manifold 1630 are fluidly coupled to the fittings 740 of the test model 700. At step 1715, a sample of the dressing 110 is wrapped around the test model 700 and the cover 125 is sealed to the test model 700 to form a sealed space containing the tissue interface 120. At step 1720, the tissue interface 120 is fluidly coupled to the negative-pressure source 105 using the fluid conductor 1315 and the dressing interface 1320. At step 1725, the restricted air flow rate (RF) through the channels 735 of the test model 700 is measured using the air flow meter 1625 prior to the application of negative pressure to the dressing 110. The restricted air flow rate (RF) may be recorded. At step 1730, negative pressure is applied to the tissue interface 120 until a target negative pressure within the tissue interface 120 of about 100 mmHg is reached. At step 1735, the air flow rate under negative pressure (NPF) through the channels 735 of the test model 700 is measured using the air flow meter 1625. The air flow rate under negative pressure (NPF) may be recorded. When negative pressure is applied to the dressing 110, the first manifold layer 405 contracts outward, creating a lifting force on the body 705 of the test model 700, which results in the air flow rate under negative pressure (NPF) to be greater than the restricted flow rate (RF). At step 1740, the negative-pressure source 105 is turned off and the pressure inside the dressing 110 may be allowed to decay to ambient pressure. In some embodiments, steps 1725, 1730, 1735, and 1740 may be repeated with the same dressing 110 (e.g., three or more times) and the values for the restricted air flow rate (RF) and the air flow rate under negative pressure (NPF) may be averaged for each sample of dressing 110. The method 1700 may then be repeated for each sample of dressing 110 to be tested.

For each sample of dressing 110 tested, the performance of the dressing 110 may be evaluated using the measured free flow rate (RF), the restricted air flow rate (RF), and the air flow rate under negative pressure (NPF). The following formulas may be used to compare the performance of the samples of the dressing 110. A scale factor may be calculated using:

$$\text{Scale} = FF - RF$$

The difference ($\Delta_{flow}$) in flow rate between the air flow rate under negative pressure (NPF) and the restricted air flow rate (RF) may be calculated using:

$$\Delta_{flow} = NPF - RF$$

The percent increase in flow rate may be calculated using:

$$\text{Increase }(\%) = \left(\frac{\Delta_{flow}}{RF}\right) \times 100 = \left(\frac{NPF - RF}{RF}\right) \times 100$$

The percent improvement in flow rate may be calculated using:

$$\text{Improvement }(\%) = \left(\frac{\Delta_{flow}}{\text{Scale}}\right) \times 100 = \left(\frac{NPF - RF}{FF - RF}\right) \times 100$$

In some embodiments, the performance of the dressing 110 may be calculated on a per channel 735 basis. In some embodiments, the performance of the dressing 110 may be calculated based on flow rates averaged across one or more of the channels 735.

FIG. 18A and FIG. 18B are tables of material properties and performance data of example configurations of the dressing 110 of FIG. 13 using the test setup of FIG. 16. Twenty samples were tested (Samples 5-24). The dressing 110 of Sample 5 only included the first manifold layer 405 and the cover 125, wherein the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm². Sample 5 showed a percent improvement of simulated lymphatic flow of 1.12%. Sample 5 was used to establish a baseline. The dressings 110 of Samples 6-24 are illustrative of a dressing having features analogous or similar to the example of FIG. 13, including the first manifold layer 405 and the support layer 1300. How-ever, for testing purposes, Samples 6-24 only included the first manifold layer 405, the support layer 1300, and the cover 125, wherein the first manifold layer 405 was the same as the first manifold layer 405 of Sample 5 and the support layer 1300 comprised the various materials having the material descriptions and properties identified in FIG. 18A and FIG. 18B. That is, the material of the first manifold layer 405 was held constant for Samples 5-24. FIG. 18A and FIG. 18B also summarize the results of the test.

In Sample 6, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a neoprene foam perforated with 6.35 millimeter apertures with 25.4 millimeter center-to-center spacing having a stiffness of 1446 gram-force (tested per ASTM D6828-02), an average thickness of 1.96 millimeters, a density of 0.11 g/cc, and a weight per unit area of 0.02 g/cm². Sample 6 had a 44.30% improvement in simulated lymphatic flow.

In Sample 7, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a pique knit polyester fabric having a stiffness of 5.5 gram-force (tested per ASTM D6828-02), an average thickness of 0.59 millimeters, a density of 0.21 g/cc, and a weight per unit area of 0.01 g/cm². Sample 7 had a 9.06% improvement in simulated lymphatic flow.

In Sample 8, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a jersey knit blend of about 21% polyester, about 65% nylon, and about 14% spandex having a stiffness of 40.5 gram-force (tested per ASTM D6828-02), an average thickness of 1.06 millimeters, a density of 0.26 g/cc, and a weight per unit area of 0.03 g/cm². Sample 8 had a 9.23% improvement in simulated lymphatic flow.

In Sample 9, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a 1×1 plain weave blend of about 65% polyester and about 35% cotton having a stiffness of 12.2 gram-force (tested per ASTM D6828-02), an average thickness of 0.30 millimeters, a density of 0.43 g/cc, and a weight per unit area of 0.01 g/cm². Sample 9 had a 10.45% improvement in simulated lymphatic flow.

In Sample 10, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a 3×1 twill weave blend of about 65% polyester and about 35% cotton having a stiffness of 69.9 gram-force (tested per ASTM D6828-02), an average thickness of 0.58 millimeters, a density of 0.47 g/cc, and a weight per unit area of 0.03 g/cm². Sample 10 had a 22.27% improvement in simulated lymphatic flow.

In Sample 11, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a 1×1 plain weave of polyester coated with polyurethane having a stiffness of 1220 gram-force (tested per ASTM D6828-02), an average thickness of 0.93 millimeters, a density of 0.26 g/cc, and a weight per unit area of 0.02 g/cm². Sample 11 had a 38.38% improvement in simulated lymphatic flow.

In Sample 12, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised an 8 gauge polyvinyl chloride film perforated with 6.35 millimeter apertures with 25.4 millimeter center-to-center spacing having a stiffness of 57.3 gram-force (tested per ASTM D6828-02), an average thickness of 0.11 millimeters, a density of 1.14 g/cc, and a weight per unit area of 0.01 g/cm². Sample 12 had a 4.56% improvement in simulated lymphatic flow.

In Sample 13, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a 16 gauge polyvinyl chloride film perforated with 6.35 millimeter apertures with 25.4 millimeter center-to-center spacing having a stiffness of 840 gram-force (tested per ASTM D6828-02), an average thickness of 0.30 millimeters, a density of 1.27 g/cc, and a weight per unit area of 0.04 g/cm². Sample 13 had a 14.78% improvement in simulated lymphatic flow.

In Sample 14, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a 20 gauge polyvinyl chloride film perforated with 6.35 millimeter apertures with 25.4 millimeter center-to-center spacing having a stiffness of 1582 gram-force (tested per ASTM D6828-02), an average thickness of 0.37 millimeters, a density of 1.29 g/cc, and a weight per unit area of 0.05 g/cm². Sample 14 had a 26.84% improvement in simulated lymphatic flow.

In Sample 15, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a glass fabric coated with polytetrafluoroethylene (PTFE) resin perforated with 6.35 millimeter apertures with 25.4 millimeter center-to-center spacing having a stiffness of 1490 gram-force (tested per ASTM D6828-02), an average thickness of 0.23 millimeters, a density of 2.10 g/cc, and a weight per unit area of 0.05 g/cm². Sample 15 had a 42.09% improvement in simulated lymphatic flow.

In Sample 16, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a glass fabric coated with polytetrafluoroethylene (PTFE) resin perforated with 6.35 millimeter apertures with 25.4 millimeter center-to-center spacing having a stiffness of 11486 gram-force (tested per ASTM D6828-02), an average thickness of 1.45 millimeters, a density of 0.82 g/cc, and a weight per unit area of 0.12 g/cm². Sample 16 had a 43.21% improvement in simulated lymphatic flow.

In Sample 17, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a polyurethane foam grid mesh having a square grid having a stiffness of 222.75 gram-force (tested per ASTM D6828-02), an average thickness of 2.57 millimeters, a density of 0.08 g/cc, and a weight per unit area of 0.02 g/cm². Sample 17 had a 4.59% improvement in simulated lymphatic flow.

In Sample 18, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a multifilament nylon PA66 mesh having a square grid having a stiffness of 51.25 gram-force (tested per ASTM D6828-02), an average thickness of 0.33 millimeters, a density of 0.09 g/cc, and a weight per unit area of 0.0029 g/cm². Sample 18 had a 20.25% improvement in simulated lymphatic flow.

In Sample 19, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a resorcinol formaldehyde latex coated glass mesh having a square grid having a stiffness of 834.75 gram-force (tested per ASTM D6828-02), an average thickness of 0.37 millimeters, a density of 0.29 g/cc, and a weight per unit area of 0.01 g/cm². Sample 19 had a 31.21% improvement in simulated lymphatic flow.

In Sample 20, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a non-woven polyester fabric having a square grid having a stiffness of 359.5 gram-force (tested per ASTM D6828-02), an average thickness of 2.50 millimeters, a density of 0.11 g/cc, and a weight per unit area of 0.03 g/cm². Sample 20 had a 16.46% improvement in simulated lymphatic flow.

In Sample 21, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised a non-woven polyester fabric that has been heat pressed for one minute at about 375 degrees Fahrenheit having a stiffness of 725 gram-force (tested per ASTM D6828-02), an average thickness of 2.03 millimeters, a density of 0.10 g/cc, and a weight per unit area of 0.02 g/cm². Sample 21 had a 35.02% improvement in simulated lymphatic flow.

In Sample 22, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised acrylonitrile butadiene rubber perforated with 6.35 millimeter apertures with 25.4 millimeter center-to-center spacing having a stiffness of 282 gram-force (tested per ASTM D6828-02), an average thickness of 0.58 millimeters, a density of 1.53 g/cc, and a weight per unit area of 0.09 g/cm². Sample 22 had an 8.44% improvement in simulated lymphatic flow.

In Sample 23, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised acrylonitrile butadiene rubber perforated with 6.35 millimeter apertures with 25.4 millimeter center-to-center spacing having a stiffness of 846 gram-force (tested per ASTM D6828-02), an average thickness of 1.77 millimeters, a density of 0.98 g/cc, and a weight per unit area of 0.17 g/cm². Sample 23 had a 29.88% improvement in simulated lymphatic flow.

In Sample 24, the first manifold layer 405 comprised an open-cell foam such as a reticulated polyurethane foam (e.g., GRANUFOAM™) having a stiffness of 910 gram-force (tested per ASTM D6828-02), an average thickness of 6.35 millimeters, a density of 0.02 g/cc, and a weight per unit area of 0.02 g/cm², and the support layer 1300 comprised acrylonitrile butadiene rubber perforated with 6.35 millimeter apertures with 25.4 millimeter center-to-center spacing having a stiffness of 2326 gram-force (tested per ASTM D6828-02), an average thickness of 1.57 millimeters, a density of 1.53 g/cc, and a weight per unit area of 0.24 g/cm². Sample 24 had a 34.75% improvement in simulated lymphatic flow.

As shown in FIG. 18A and FIG. 18B, increased performance occurred with a stiffer outer layer. For example, Samples 6, 11, 14, 15, 16, and 24 of dressings 110 having support layers 1300 comprising materials having a stiffness greater than 1000 gram-force (gf) resulted in percent improvements of simulated lymphatic flow greater than 25%. Samples 6, 11, 15, 16, and 24 of dressings 110 having support layers 1300 comprising materials having a stiffness greater than 1200 gram-force (gf) resulted in percent improvements of simulated lymphatic flow greater than 30%. Samples 6, 15, and 16 of dressings 110 having support layers 1300 comprising materials having a stiffness greater than 1400 gram-force (gf) resulted in percent improvements of simulated lymphatic flow greater than 40%. For example, Sample 6 of dressing 110 having a support layer 1300 comprising a material having a stiffness of 1446 gram-force (gf) resulted in about a 44.30 percent improvement of simulated lymphatic flow. As shown in FIG. 18A and FIG. 18B, as stiffness of the support layer 1300 increases the simulated lymphatic flow generally increases. Simulated lymphatic flow percent increases in a range of about 42.09% to about 44.30% were found to be with the stiffness of the support layer 1300 being in a range of about 1446 gram-force to about 1490 gram-force (Samples 6 and 15). Beyond a certain threshold stiffness, the percent improvement of simulated lymphatic flow does not significantly improve. For example, Sample 16 included a support layer 1300 having a stiffness of 11486 gram-force but did not provide an increase in simulated lymphatic flow over Sample 6 with a support layer 1300 having a stiffness of 1446 gram-force. Additionally, some samples with a support layer 1300 having a higher stiffness and a higher weight per unit area did not perform as well as other samples with a support layer 1300 having a high stiffness and a lower weight per unit area. For example, Sample 24 with a support layer 1300 having a stiffness of 2326 gram-force and a weight per unit area of 0.24 g/cm² had a lower percent improvement of simulated lymphatic flow than Sample 6 with a support layer 1300 have a lower stiffness of 1446 gram-force and a lower weight per unit area of 0.02 g/cm². Accordingly, a support layer 1300 having a high weight per unit area may result in a lesser percent improvement than a less stiff support layer 1300 that has a lower weight per unit area.

Additionally, as can be seen in FIG. 18, the size or density of the apertures 1305 in the support layers 1300 did not appear to have a detrimental impact on the percent improvement of simulated lymphatic flow. For example, Sample 6 with a support layer 1300 comprising neoprene foam perforated with about 6.35 millimeter apertures 1305 with about a 25.4 millimeter center-to-center spacing had a 44.30% improvement of simulated lymphatic flow. Additionally, Sample 6 with a support layer 1300 comprising a composite film of glass fabric coated with polytetrafluoroethylene (PTFE) resin perforated with about 6.35 millimeter apertures 1305 with about a 25.4 millimeter center-to-center spacing had a 42.09% improvement of simulated lymphatic flow. In some embodiments, no reduction in the improvement of simulated lymphatic flow was observed in a dressing 110 with a support layer 1300 circumferentially covering the first manifold layer 405 and having an array of apertures 1305 with an open area less than 50%.

Figure 19:
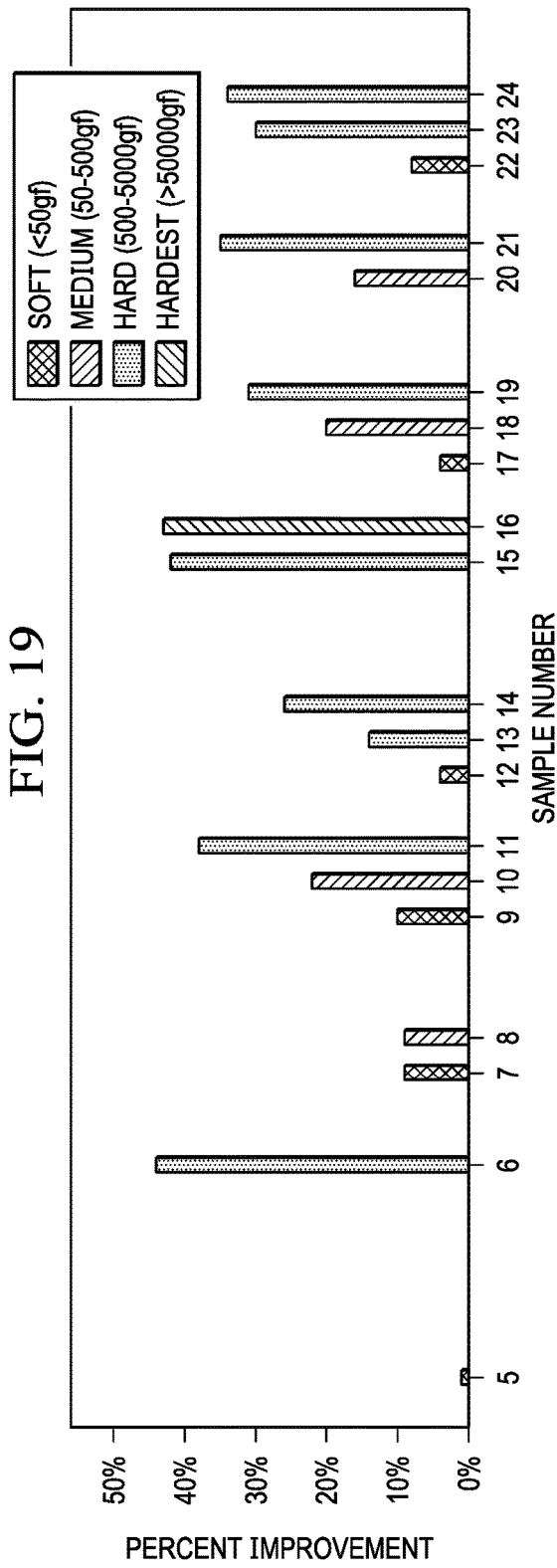
FIG. 19 is a bar chart of performance data of example configurations of the dressing of FIG. 13 using the test setup of FIG. 16.
Figure 20:
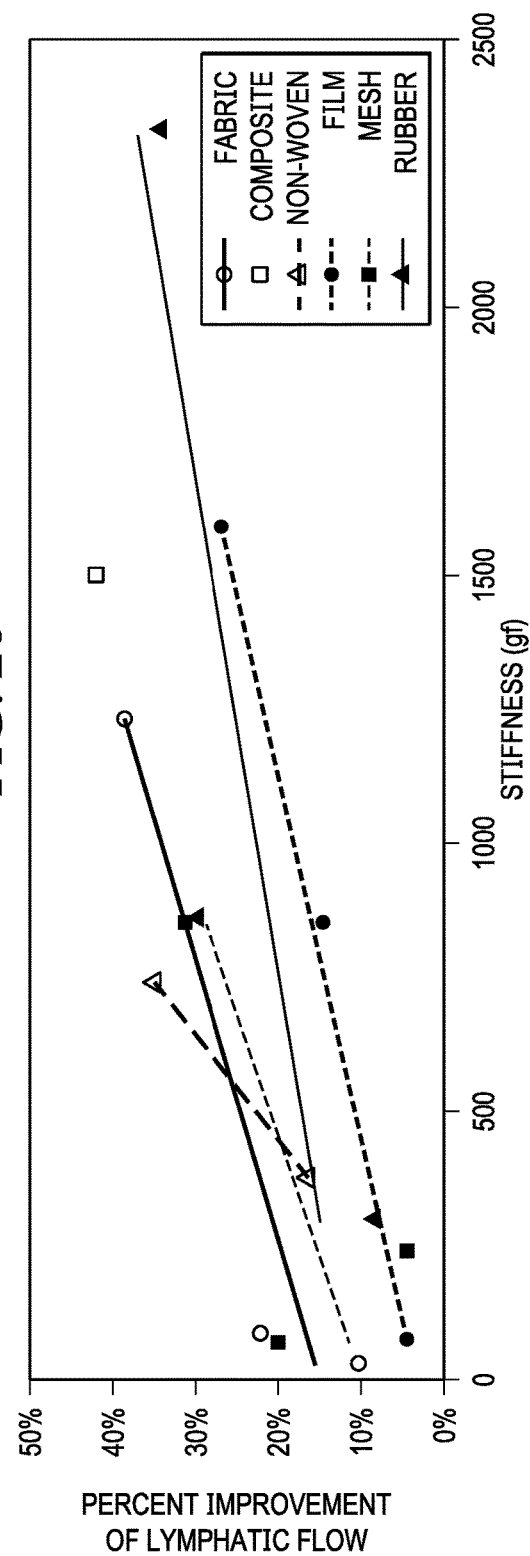
FIG. 20 is a plot of performance data of example configurations of the dressing of FIG. 13 using the test setup of FIG. 16.

FIG. 19 is a bar chart of the data of FIG. 18 wherein the Sample number is along the x-axis and the percent improvement is along the y-axis. FIG. 20 is a plot of performance data of example configurations of the dressing of FIG. 13 using the test setup of FIG. 16. In FIG. 20, the stiffness of the support layer 1300 is along the x-axis and the percent improvement of lymphatic flow is along the y-axis. As shown in FIG. 20, the percent improvement of lymphatic flow increases generally linearly with increasing stiffness within the same type of material; however, the slopes of different materials are different.

The systems, apparatuses, and methods described herein may provide significant advantages. For example, some embodiments of the dressing 110 may provide effective incision management while simultaneously providing the additional benefits of negative pressure over surrounding tissue to improve circulation through the subcutaneous lymph vascular network, reduce edema, improve perfusion, and reduce risk of post-operative complications such as infection, seroma, hematoma, and dehiscence. Some embodiments of the dressing 110 may be particularly effective for treating a curved tissue site, such as a breast, a shoulder, an arm, a leg, a knee joint, or an ankle joint. Circumferential dressings 110 with a support layer 1300 may reduce swelling via improved decompression of localized tissues. More rapid and effective reduction in swelling may be key to many clinical benefits. Additionally, decompression therapy provided by the dressing 110 may be adapted into the current standard of care as an improvement over the current Rest, Ice, Compression, and Elevation (RICE) protocol or other existing therapies.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for promoting circulation through a subcutaneous lymph vascular network, the apparatus comprising:
   a manifold layer having a first stiffness, the first stiffness is from about 800 gram-force to about 1000 gram-force;
   a support layer adjacent to the manifold layer, the support layer comprising one or more apertures, and the support layer having a second stiffness greater than the first stiffness;
   a cover adjacent to the support layer; and
   a fluid interface configured to fluidly couple at least one of the manifold layer and the support layer to a fluid conductor;
   wherein when negative pressure is applied to one or more of the manifold layer and the support layer at least a portion of the apertures are visible through the cover.

2. The apparatus of claim 1, wherein when negative pressure is applied to one or more of the manifold layer and the support layer at least a portion of the cover is configured to be drawn into the one or more apertures to form one or more indentations.

3. The apparatus of claim 2, wherein the indentations are visible.

4. The apparatus of claim 1, wherein the second stiffness is at least 1.3 times greater than the first stiffness.

5. The apparatus of claim 1, wherein:
   the manifold layer has a first thickness; and
   the support layer has a second thickness less than the first thickness.

6. The apparatus of claim 1, wherein the manifold layer comprises open-cell foam.

7. The apparatus of claim 1, wherein the first stiffness is about 910 gram-force.

8. The apparatus of claim 1, wherein the second stiffness is from about 800 gram-force to about 3000 gram-force.

9. The apparatus of claim 1, wherein the second stiffness is from about 800 gram-force to about 2000 gram-force.

10. The apparatus of claim 1, wherein the second stiffness is from about 1000 gram-force to about 2000 gram-force.

11. The apparatus of claim 1, wherein the second stiffness is from about 1200 gram-force to about 1500 gram-force.

12. The apparatus of claim 1, wherein the support layer comprises a closed-cell foam.

13. The apparatus of claim 1, wherein the support layer comprises neoprene foam.

14. The apparatus of claim 1, wherein the support layer comprises a knit fabric.

15. The apparatus of claim 1, wherein the support layer comprises a woven fabric.

16. The apparatus of claim 1, wherein the support layer comprises a polyvinyl chloride film.

17. The apparatus of claim 1, wherein the support layer comprises a composite film.

18. The apparatus of claim 1, wherein the support layer comprises a non-woven fabric.

19. The apparatus of claim 1, wherein the support layer comprises rubber.

20. An apparatus for promoting circulation through a subcutaneous lymph vascular network, the apparatus comprising:
   a manifold layer having a first stiffness, wherein the first stiffness is from about 800 gram-force to about 1000 gram-force;
   a support layer adjacent to the manifold layer, the support layer having a second stiffness greater than the first stiffness; and
   a fluid interface configured to fluidly couple at least one of the manifold layer and the support layer to a fluid conductor.

21. The apparatus of claim 20, further comprising a cover adjacent to the support layer, and wherein the support layer comprises one or more apertures.

22. The apparatus of claim 21, wherein when negative pressure is applied to one or more of the manifold layer and the support layer at least a portion of the apertures are visible through the cover.

23. The apparatus of claim 21, wherein when negative pressure is applied to one or more of the manifold layer and the support layer at least a portion of the cover is configured to be drawn into the one or more apertures to form one or more indentations.

24. The apparatus of claim 20, wherein the first stiffness is about 910 gram-force.

25. The apparatus of claim 20, wherein the second stiffness is from about 800 gram-force to about 3000 gram-force.

26. The apparatus of claim 20, wherein the second stiffness is from about 800 gram-force to about 2000 gram-force.

27. The apparatus of claim 20, wherein the second stiffness is from about 1000 gram-force to about 2000 gram-force.

28. The apparatus of claim 20, wherein the second stiffness is from about 1200 gram-force to about 1500 gram-force.

29. The apparatus of claim 20, wherein:
   the manifold layer has a first thickness; and
   the support layer has a second thickness less than the first thickness.

30. The apparatus of claim 20, wherein the support layer comprises a closed-cell foam.

31. The apparatus of claim 20, wherein the support layer comprises neoprene foam.

32. The apparatus of claim 20, wherein the support layer comprises a knit fabric.

33. The apparatus of claim 20, wherein the support layer comprises a woven fabric.

34. The apparatus of claim 20, wherein the support layer comprises a polyvinyl chloride film.

35. The apparatus of claim 20, wherein the support layer comprises a composite film.

36. The apparatus of claim 20, wherein the support layer comprises rubber.

37. An apparatus for promoting circulation through a subcutaneous lymph vascular network, the apparatus comprising:
   a manifold layer having a first stiffness;
   a support layer adjacent to the manifold layer, the support layer having a second stiffness greater than the first stiffness, wherein the second stiffness is from about 800 gram-force to about 3000 gram-force; and
   a fluid interface configured to fluidly couple at least one of the manifold layer and the support layer to a fluid conductor.

38. The apparatus of claim 37, further comprising a cover adjacent to the support layer, and wherein the support layer comprises one or more apertures.

39. The apparatus of claim 38, wherein when negative pressure is applied to one or more of the manifold layer and the support layer at least a portion of the apertures are visible through the cover.

40. The apparatus of claim 38, wherein when negative pressure is applied to one or more of the manifold layer and the support layer at least a portion of the cover is configured to be drawn into the one or more apertures to form one or more indentations.

41. The apparatus of claim 37, wherein the second stiffness is from about 800 gram-force to about 2000 gram-force.

42. The apparatus of claim 37, wherein the second stiffness is from about 1000 gram-force to about 2000 gram-force.

43. The apparatus of claim 37, wherein the second stiffness is from about 1200 gram-force to about 1500 gram-force.

44. The apparatus of claim 37, wherein:
   the manifold layer has a first thickness; and
   the support layer has a second thickness less than the first thickness.

45. The apparatus of claim 37, wherein the support layer comprises a closed-cell foam.

46. The apparatus of claim 37, wherein the support layer comprises neoprene foam.

47. The apparatus of claim 37, wherein the support layer comprises a knit fabric.

48. The apparatus of claim 37, wherein the support layer comprises a woven fabric.

49. The apparatus of claim 37, wherein the support layer comprises a polyvinyl chloride film.

50. The apparatus of claim 37, wherein the support layer comprises a composite film.

51. The apparatus of claim 37, wherein the support layer comprises rubber.

* * * * *